(12) United States Patent
Zhu

(10) Patent No.: US 11,642,335 B2
(45) Date of Patent: May 9, 2023

(54) CHEMICAL SYNTHESIS OF CLOPIDOGREL ACTIVE METABOLITES AND DISULFIDE CONJUGATE PRODRUGS

(71) Applicant: Board of Regents, The University of Texas System, Austin, TX (US)

(72) Inventor: Yaoqiu Zhu, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 113 days.

(21) Appl. No.: 17/034,228

(22) Filed: Sep. 28, 2020

(65) Prior Publication Data
US 2021/0093624 A1    Apr. 1, 2021

Related U.S. Application Data

(60) Provisional application No. 62/906,644, filed on Sep. 26, 2019.

(51) Int. Cl.
| | | |
|---|---|---|
| *C07D 211/96* | (2006.01) | |
| *A61K 31/45* | (2006.01) | |
| *A61K 31/4353* | (2006.01) | |

(52) U.S. Cl.
CPC ............ *A61K 31/45* (2013.01); *C07D 211/96* (2013.01); *A61K 31/4353* (2013.01)

(58) Field of Classification Search
None
See application file for complete search history.

(56) References Cited

U.S. PATENT DOCUMENTS 6,610,708 B1 * 8/2003 Asai ...................... C07D 471/08
514/327

FOREIGN PATENT DOCUMENTS

| CN | 102911173 A | 2/2013 | | |
|---|---|---|---|---|
| WO | WO-2014109987 A1 | * | 7/2014 | ........... A61K 31/445 |
| WO | WO-2016176644 A1 | * | 11/2016 | ........... A61K 31/445 |

OTHER PUBLICATIONS

Food and Drug Administration (FDA), Plavix (clopidogrel bisulfate tablets) label and prescription information. Available at: https://www.accessdata.fda.gov/drugsatfda_docs/label/2016/020839s062s064lbl.pdf. Revised Sep. 2016.
Savi, P., Nurden, P., Nurden, A. T., Levy-Toledano, S., Herbert, J. M. Clopidogrel: a review of its mechanism of action. Platelets 1998, 9, 251-255 (Abstract Only).
Savi, P., Herbert, J. M. Clopidogrel and ticlopidine: P2Y12 adenosine diphosphate-receptor antagonists for the prevention of atherothrombosis. Semin. Thromb. Hemost. 2005, 31, 174-183 (Abstract Only).
Gouya, G., Arrich, J., Wolzt, M., Huber, K., Verheugt, F. W., Gurbel, P. A., Pirker-Kees, A., Siller-Matula, J. M. Antiplatelet treatment for prevention of cerebrovascular events in patients with vascular diseases: a systematic review and metaanalysis. Stroke 2014, 45, 492-503 (Abstract Only).
Caldeira, D., Fernandes, R. M., Costa, J., David, C., Sampaio, C., Ferreira, J. J. Branded versus generic clopidogrel in cardiovascular diseases: a systematic review. J. Cardiovasc. Pharmacol. 2013, 61, 277-282 (Abstract Only).
Gurbel, P. A., Bliden, K.P., Hiatt, B. L., O'Connor, C. M. Clopidogrel for coronary stenting: response variability, drug resistance, and the effect of pretreatment platelet reactivity. Circulation 2003, 107, 2908-2913 (Abstract Only).
Kolandaivelu, K., Bhatt, D. L. Overcoming 'resistance' to antiplatelet therapy: targeting the issue of nonadherence. Nat. Rev. Cardiol. 2010, 7, 461 (Abstract Only).
Food and Drug Administration (FDA), Drug Safety Communication: reduced effectiveness of Plavix (clopidogrel) in patients who are poor metabolizers of the drug. Available at: http://www.fda.gov/Drugs/DrugSafety/PostmarketDrugSafetyInformationforPatientsandProviders/ucm203888.htm. Accessed Apr. 28, 2010.
Holmes, D. R. Jr., Dehmer, G. J., Kaul, S., Leifer, D., O'Gara, P. T., Stein, C. M. ACCF/AHA clopidogrel clinical alert: approaches to the FDA "boxed warning": a report of the American College of Cardiology Foundation Task Force on clinical expert consensus documents and the American Heart Association endorsed by the Society for Cardiovascular Angiography and Interventions and the Society of Thoracic Surgeons. J. Am. Coll. Cardiol. 2010, 56, 321341.
Savi, P., Pereillo, J. M., Uzabiaga, M. F., Combalbert, J., Picard, C., Maffrand, J. P., Pascal, M., Herbert, J. M. Identification and biological activity of the active metabolite of clopidogrel. Thromb. Haemost. 2000, 84, 891-896 (Abstract Only).
Pereillo, J. M., Maftouh, M., Andrieu, A., Uzabiaga, M. F., Fedeli, O., Savi, P., Pascal, M., Herbert, J. M., Maffrand, J. P., Picard, C. Structure and stereochemistry of the active metabolite of clopidogrel. Drug Metab. Dispos. 2002, 30, 1288-1295 (Abstract Only).
Dansette, P. M., Libraire, J., Bertho, G., Mansuy, D. Metabolic oxidative cleavage of thioesters: evidence for the formation of sulfenic acid intermediates in the bioactivation of the antithrombotic prodrugs ticlopidine and clopidogrel. Chem. Res. Toxicol. 2009, 22, 369-373 (Abstract Only).
Dansette, P. M., Rosi, J., Bertho, G., Mansuy, D. Paraoxonase-1 and clopidogrel efficacy. Nat. Med. 2011, 17, 1040-1041 (No Abstract Available).
Dansette, P. M., Rosi, J., Bertho, G., Mansuy, D. Cytochromes P450 catalyze both steps of the major pathway of clopidogrel bioactivation, whereas paraoxonase catalyzes the formation of a minor thiol metabolite isomer. Chem. Res. Toxicol. 2012, 25, 348-356 (Abstract Only).
Hagihara, K., Kazui, M., Kurihara, A., Yoshiike, M., Honda, K., Okazaki, O., Farid, N. A., Ikeda, T. A possible mechanism for the differences in efficiency and variability of active metabolite formation from thienopyridine antiplatelet agents, prasugrel and clopidogrel. Drug Metab. Dispos. 2009, 37, 2145-2152 (Abstract Only).

(Continued)

*Primary Examiner* — Amanda L. Aguirre
(74) *Attorney, Agent, or Firm* — Yee & Associates, P.C.

(57) ABSTRACT

A method of synthesizing a clopidogrel metabolite is provided. A piperidone intermediate is formed from a mandelate. An asymmetric ketone reduction of the piperidone intermediate is performed. A mercapto installation is performed on the piperidone intermediate to form a clopidogrel metabolite that includes a 4-carbon chiral center having an (R) configuration.

1 Claim, 16 Drawing Sheets

(56) References Cited

OTHER PUBLICATIONS

Zhu, Y., Zhou, J. Identification of the significant involvement and mechanistic role of CYP3A4/5 in clopidogrel bioactivation. ACS Med. Chem. Lett. 2012, 3 (Abstract Only).
Zhu, Y., Zhou, J. In vitro biotransformation studies of 2-oxo-clopidogrel: multiple thiolactone ring-opening pathways further attenuate prodrug activation. Chem. Res. Toxicol. 2013, 26, 179-190 (Abstract Only).
Savi, P., Zachayus, J. L., DelesqueTouchard, N., Labouret, C., Herve, C., Uzabiaga, M. F., Pereillo, J. M., Culouscou, J. M., Bono, F., Ferrara, P., Herbert, J. M. The active metabolite of Clopidogrel disrupts P2Y12 receptor oligomers and partitions them out of lipid rafts. Proc. Natl. Acad. Sci. U.S.A. 2006, 103, 11069-11074 (Abstract Only).
Zhang, K., Zhang, J., Gao, Z. G., Paoletta, S., Zhang, D., Han, G. W., Li, T., Ma. L., Zhang, W., Müller, C. E., Yang, H., Jiang, H., Cherezov, V., Katritch, V., Jacobson, K. A., Stevens, R. C., Wu, B., Zhao, Q. Agonist-bound structure of the human P2Y12 receptor. Nature 2014, 509, 119-122 (Abstract Only).
Kazui, M., Nishiya, Y., Ishizuka, T., Hagihara, K., Farid, N. A., Okazaki, O., Ikeda, T., Kurihara, A. Identification of the human cytochrome P450 enzymes involved in the two oxidative steps in the bioactivation of clopidogrel to its pharmacologically active metabolite. Drug Metab. Dispos. 2010, 38, 92-99 (Astract Only).
Mega, J. L., Close, S. L., Wiviott, S. D., Shen, L., Hockett, R. D., Brandt, J. T., Walker, J. R., Antman, E. M., Macias, W., Braunwald, E., Sabatine, M. S. Cytochrome P-450 polymorphisms and response to clopidogrel. N. Engl. J. Med. 2009, 360, 354-362 (Abstract Only).
Hochholzer, W., Trenk, D., Fromm, M. F., Valina, C. M., Stratz, C., Bestehom, H. P., Büttner, H. J., Neumann, F. J. Impact of cytochrome P450 2C19 loss-of-function polymorphism and of major demographic characteristics on residual platelet function after loading and maintenance treatment with clopidogrel in patients undergoing elective coronary stent placement. J. Am. Coll. Cardiol. 2010, 55, 2427-2434 (Abstract Only).
Gilard, M., Arnaud, B., Cornily, J. C., Le Gal, G., Lacut, K., Le Calvez, G., Mansourati, J., Mottier, D., Abgrall, J. F., Boschat, J. Influence of omeprazole on the antiplatelet action of clopidogrel associated with aspirin: the randomized, double-blind OCLA (Omeprazole CLopidogrel Aspirin) study. J. Am. Coll. Cardiol. 2008, 51, 256-260 (Abstract Only).
Bundhun, P. K., Teeluck, A. R., Bhurtu, A., Huang, W. Q. Is the concomitant use of clopidogrel and proton pump inhibitors still associated with increased adverse cardiovascular outcomes following coronary angioplasty?: a systematic review and meta-analysis of recently published studies (2012-2016). BMC Cardiovasc. Disord. 2017, 17:3.
Gong, I. Y., Crown, N., Suen, C., Schwarz, U., Dresser, G., Knauer, M., Sugiyama, D., Degorter, M., Woolsey, S., Tirana, R., Kim, R. Clarifying the importance of CYP2C19 and PON1 in the mechanism of clopidogrel bioactivation and in vivo antiplatelet response. Eur. Heart J. 2012, 33, 2856-2864.
Furlong, M. T., Savant, I., Yuan, M., Scott, L., Mylott, W., Mariannino, T., Kadiyala, P., Roongta, V., Arnold, M. E. A validated HPLC-MS/MS assay for quantifying unstable pharmacologically active metabolites of clopidogrel in human plasma: Application to a clinical pharmacokinetic study. J. Chromatogr. B 2013, 926, 36-41 (Abstract Only).
Liu, C., Lu, Y., Sun, H., Yang, J., Liu, Y., Lai, X., Gong, Y., Liu, X., Li, Y., Zhang, Y., Chen, X., Zhong, D. Development and validation of a sensitive and rapid UHPLC-MS/MS method for the simultaneous quantification of the common active and inactive metabolites of vicagrel and clopidogrel in human plasma. J. Pharm. Biomed. Anal. 2018, 149, 394-402 (Abstract Only).
Tuffal, G., Roy, S., Lavisse, M., Brasseur, D., Schofield, J., Delesque Touchard, N., Savi, P., Bremond, N., Rouchon, M. C., Hurbin, F., Sultan, E. An improved method for specific and quantitative determination of the clopidogrel active metabolite isomers in human plasma. Thromb. Haemost. 2011, 105, 696-705 (Abstract Only).
Bluet, G., Blankenstein, J., Brohan, E., Prévost, C., Chevé, M., Schofield, J., Roy, S. Synthesis of the stabilized active metabolite of clopidogrel. Tetrahedron 2014, 70, 3893-3900.
Zhang, H., Lauver, D. A., Lucchesi, B. R., Hollenberg, P. F. Formation, reactivity, and antiplatelet activity of mixed disulfide conjugates of clopidogrel. Mol. Pharmacol. 2013, 83, 848-856 (Abstract Only).
Zhang, H., Lauver, D. A., Hollenberg, P. F. CYP-independent inhibition of platelet aggregation in rabbits by a mixed disulfide conjugate of clopidogrel. Thromb. Haemost. 2014, 112, 1304-1311.
Zhang, H., Hollenberg, P. F. From mechanism to therapeutics: overcoming inter-individual varibility in clopidogrel therapy. In Clopidogrel: pharmacology, clinical uses and adverse effects; Alesci, J. P., Victorino, A. Ed.; New York: Nova Scientific Publisher, 2014; p. 121147.
Zhang, H., Lauver, D. A., Wang, H., Sun, D., Hollenberg, P. F., Chen, Y. E., Osawa, Y., Eitzman, D. T. Significant improvement of antithrombotic responses to clopidogrel by use of a novel conjugate as revealed in an arterial model of thrombosis. J. Pharmacol. Exp. Ther. 2016, 359, 11-17.
Lauver, D. A., Kuszynski, D. S., Christian, B. D., Bernard, M. P., Teuber, J. P., Markham, B. E., Chen, Y. E., Zhang, H. DT-678 inhibits platelet activation with lower tendency for bleeding compared to existing P2Y12 antagonists. Pharmacol. Res. Perspect. 2019, 7, e00509.
Shaw, S. A., Balasubramanian, B., Bonacorsi, S., Cortes, J. C., Cao, K., Chen, B. C., Dai, J., Decicco, C., Goswami, A., Guo, Z., Hanson, R., Humphreys, W. G., Lam, P. Y., Li, W., Mathur, A., Maxwell, B. D., Michaudel, Q., Peng, L., Pudzianowski, A., Qiu, F., Su, S., Sun, D., Tymiak, A. A., Vokits, B. P., Wang, B., Wexler, R., Wu, D. R., Zhang, Y., Zhao, R., Baran, P. S. Synthesis of biologically active piperidine metabolites of clopidogrel: determination of structure and analyte development. J. Org. Chem. 2015, 80, 7019-7032 (Abstract Only).
Corey, E. J., Helal, C. J. Reduction of carbonyl compounds with chiral oxazaborolidine catalysts: A new paradigm for enantioselective catalysis and a powerful new synthetic method. Angew. Chem. Int. Ed. 1998, 37, 1986-2012 (Abstract Only).
Zhang, H.-C., Harris, B. D., Costanzo, M. J., Lawson, E. C., Maryanoff, C. A., Maryanoff, B. E. Stereocontrol between remote atom centers in acyclic substrates. Anti addition of hydride to 1,5-, 1,6-, and 1,7-hydroxy ketones. J. Org. Chem. 1998, 63, 7964-7981 (Abstract Only).
Salles, H., Whiting, A. The control of remote asymmetric centres via reduction of acyclic carbonyl functions. J. Chem. Soc., Perkin Trans. 1 2000, 1785-1805 (Abstract Only).
Allen, C. F. H., Fournier, J. O., Humphlett, W. J. The thermal reversibility of the Michael reaction: IV. Thiol adducts. Can. J. Chem. 1964, 42, 2616.
Krenske, E. H., Petter, R. C., Houk, K. N. Kinetics and thermodynamics of reversible thiol additions to mono- and diactivated Michael acceptors: Implications for the design of drugs that bind covalently to cysteines. J. Org. Chem. 2016, 81, 11726-11733 (Abstract Only).
Dansette, P. M., Levent, D., Hessani, A., Mansuy, D. Bioactivation of clopidogrel and prasugrel: Factors determining the stereochemistry of the thiol metabolite double bond. Chem. Res. Toxicol. 2015, 28, 1338-1345 (Abstract Only).
Liu, C., Chen, Z., Zhong, K., Li, L., Zhu, W., Chen, X., Zhong, D. Human liver cytochrome P450 enzymes and microsomal thiol methyltransferase are involved in the stereoselective formation and methylation of the pharmacologically active metabolite of clopidogrel. Drug Metab. Dispos. 2015, 43, 1632-1641 (Abstract Only).
Wang, Y., Sun, Y., Li, D., Zhang, L., Wang, K., Zuo, Y., et al. Platelet P2Y12 is involved in murine pulmonary metastasis. PLoS One 2013, 8, e80780.
Gebremeskel, S., LeVatte, T., Liwski, R. S., Johnston, B., Bezuhly, M. The reversible P2Y12 inhibitor ticagrelor inhibits metastasis and improves survival in mouse models of cancer. Int. J. Cancer 2015, 136, 234-240.
Cho, M. S., Noh, K., Haemmerle, M., Li, D., Park, H., Hu, Q., Hisamatsu, T., Mitamura, T., Mak, S. L. C., Kunapuli, S., Ma, Q.,

(56) References Cited

OTHER PUBLICATIONS

Sood, A. K., AfsharKharghan, V. Role of ADP receptors on platelets in the growth of ovarian cancer. Blood 2017, 130, 1235-1242 (Abstract).
Ballerini, P., Dovizio, M., Bruno, A., Tacconelli, S., Patrignani, P. P2Y12 receptors in tumorigenesis and metastasis. Front. Pharmacol. 2018, 9, 66 (Abstract).
Haynes, S. E., Hollopeter, G., Yang, G., Kurpius, D., Dailey, M. E., Gan, W. B., Julius, D. The P2Y12 receptor regulates microglial activation by extracellular nucleotides. Nat. Neurosci. 2006, 9, 1512-1519 (Abstract).
Qin, C., Zhou, J., Gao, Y., Lai, W., Yang, C., Cai, Y., Chen, S., Du, C. Critical role of P2Y12 receptor in regulation of Th17 differentiation and experimental autoimmune encephalomyelitis pathogenesis. J. Immunol. 2017, 199, 72-81.
Muniz, V. S., Baptista-DosReis, R., Benjamim, C. F., Mata-Santos, H. A., Pyrrho, A. S., Strauch, M. A., Melo, P. A., Vicentino, A. R., Silva-Paiva, J., Bandeira-Melo, C., Weller, P. F., Figueiredo, R. T., Neves, J. S. Purinergic P2Y12 receptor activation in eosinophils and the schistosomal host response. PLoS One 2015, 10, e0139805.
Yu, W., Sun, X., Robson, S. C., Hill, W. G. ADP-induced bladder contractility is mediated by P2Y12 receptor and temporally regulated by ectonucleotidases and adenosine signaling. FASEB J. 2014, 28, 5288-5298 (Abstract).
Ding, Z., Kim, S., Dorsam, R. T., Jin, J., Kunapuli, S. P. Inactivation of the human P2Y12 receptor by thiol reagents requires interaction with both extracellular cysteine residues, Cys17 and Cys270. Blood 2003, 101, 3908-3914 (Abstract Only).
Singh, J., Petter, R. C., Baillie, T. A., Whitty, A. The resurgence of covalent drugs. Nat. Rev. Drug Discovery 2011, 10, 307- 317.
De Cesco, S., Kurian, J., Dufresne, C., Mittermaier, A., Moitessier, N. Covalent inhibitors design and discovery. Eur. J. Med. Chem. 2017, 138, 96-114 (Abstract Only).
Ghosh, A. K., Samanta, I., Mondal, A., Liu, W. R. Covalent inhibition in drug discovery. ChemMedChem 2019, 14, 889-906 (Abstract Only).
Yi, M. C., Khosla, C. Thiol-disulfide exchange reactions in the mammalian extracellular environment. Annu. Rev. Chem. Biomol. Eng. 2016, 7, 197-222.
Huang, K., Huang, L., van Breemen, R. B. Detection of reactive metabolites using isotope-labeled glutathione trapping and simultaneous neutral loss and precursor ion scanning with ultrahigh-pressure liquid chromatography triple quadruple mass spectrometry. Anal. Chem. 2015, 87, 3646-3654 (Abstract Only).
Douat, C., Berni, E., Jacquet, R., Pouységu, L., Deffieux, D., Quideau, S. Protecting-group-free solid-phase anchoring of polyphenolic C-glucosidic ellagitannins and synthesis of 1-alkylaminovescalagin derivatives. Eur. J. Org. Chem. 2014, 23, 4963-4972. (Abstract Only).
Filipovic, M. R., Zivanovic, J., Alvarez, B., Banerjee, R. Chemical Biology of H2S Signaling through Persulfidation. Chem. Rev. 2018, 118, 1253-1337. (Abstract Only).
Zhou, H., Ding, L., Wu, Z., Cao, X., Zhang, Q., Lin, L., Bian, J. S. Hydrogen sulfide reduces RAGE toxicity through inhibition of its dimer formation. Free Radic. Biol. Med. 2017, 104, 262-271. (Abstract Only).
Zagli, G., Patacchini, R., Trevisani, M., Abbate, R., Cinotti, S., Gensini, G. F., Masotti, G., Geppetti, P. Hydrogen sulfide inhibits human platelet aggregation. Eur. J. Pharmacol. 2007, 559, 6568. (Abstract Only).
Pircher, J., Fochler, F., Czermak, T., Mannell, H., Kraemer, B. F., Wörnle, M., Sparatore, A., Del Soldato, P., Pohl, U., Krötz, F. Hydrogen sulfide-releasing aspirin derivative ACS14 exerts strong antithrombotic effects in vitro and in vivo. Arterioscler. Thromb. Vasc. Biol. 2012, 32, 2884-2891. (Abstract Only).
Zhu, Y., Romero, E. L., Ren, X., Sanca, A. J., Du, C., Liu, C., Karim, Z. A., Alshbool, F. Z., Khasawneh, F. T., Zhou, J., Zhong, D., Geng, B. Clopidogrel as a donor probe and thioenol derivatives as flexible promoieties for enabling H2S biomedicine. Nat. Commun. 2018, 9, 3952 (Abstract Only).
Gurbel, P. A., Cummings, C. C., Bell, C. R., Alford, A. B., Meister, A. F., Serebruany, V. L. Onset and extent of platelet inhibition by clopidogrel loading in patients undergoing elective coronary stenting: the Plavix Reduction of New Thrombus Occurrence (PRONTO) trial. Am. Heart J. 2003, 145, 239-247. (Abstract Only).
Bellemainappaix, A., Montalescot, G., Silvain, J., Barthelemy, O., Beygui, F., Collet, J. P., Sideris, G., Meuleman, C., Bal-Dit-Sollier, C., Lellouche, N., Ducrocq, G., Slama, M., Milleron, O., Henry, P., Drouet, L. Slow response to clopidogrel predicts low response. J. Am. Coll. Cardiol. 2010, 55, 815-822. (Abstract Only).
Cattaneo, M. The platelet P2Y12 receptor for adenosine diphosphate: congenital and drug-induced defects. Blood 2011, 117, 2102-1012. (Abstract Only).
Becker, R. C., Bassand, J. P., Budaj, A., Wojdyla, D. M., James, S. K., Cornel, J. H., French, J., Held, C., Horrow, J., Husted, S., Lopez-Sendon, J., Lassila, R., Mahaffey, K. W., Storey, R. F., Harrington R. A., Wallentin, L. Bleeding complications with the P2Y12 receptor antagonists clopidogrel and ticagrelor in the PLATelet inhibition and patient Outcomes (PLATO) trial. Eur. Heart J. 2011,32, 2933-2944.
Ding, Z., Kim, S., Kunapuli, S. P. Identification of a potent inverse agonist at a constitutively active mutant of human P2Y12 receptor. Mol. Pharmacol. 2006, 69, 338-345. (Abstract Only).
Hu, L., Chang, L., Zhang, Y., Zhai, L., Zhang, S., Qi, Z., Yan, H., Yan, Y., Luo, X., Zhang, S., Wang, Y., Kunapuli, S. P., Ye, H., Ding, Z. Platelets express activated P2Y12 receptor in patients with diabetes mellitus. Circulation 2017, 136, 817-833.

\* cited by examiner

FIG. 6
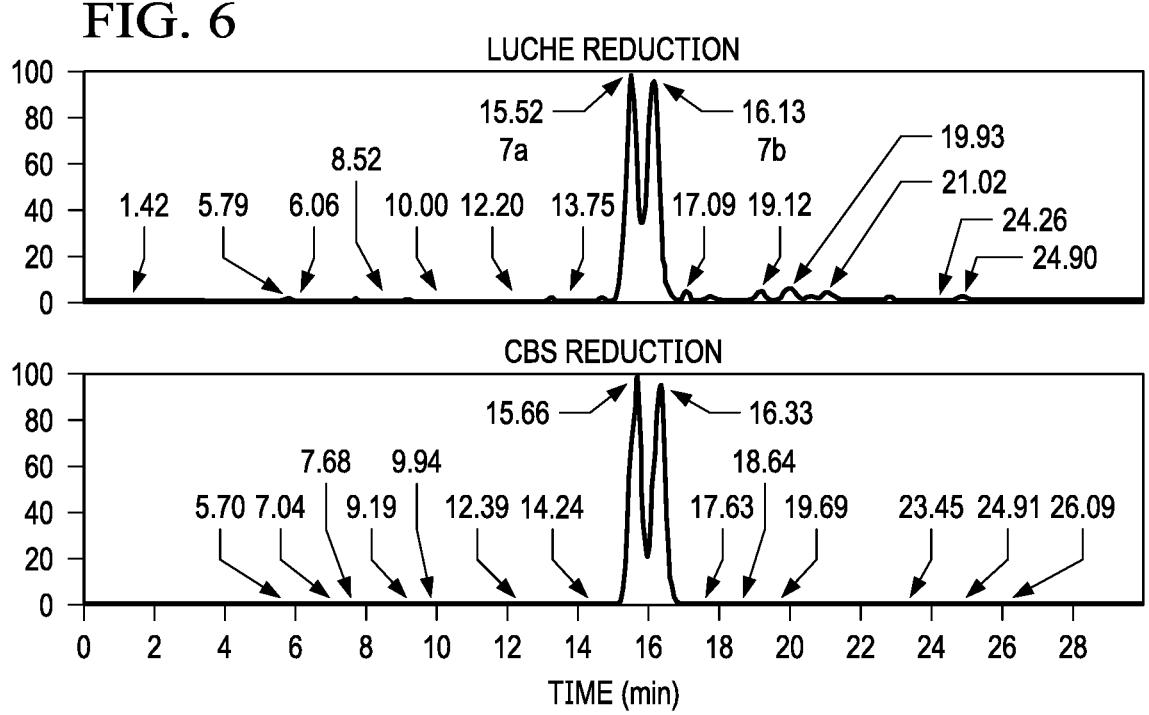
FIG. 7
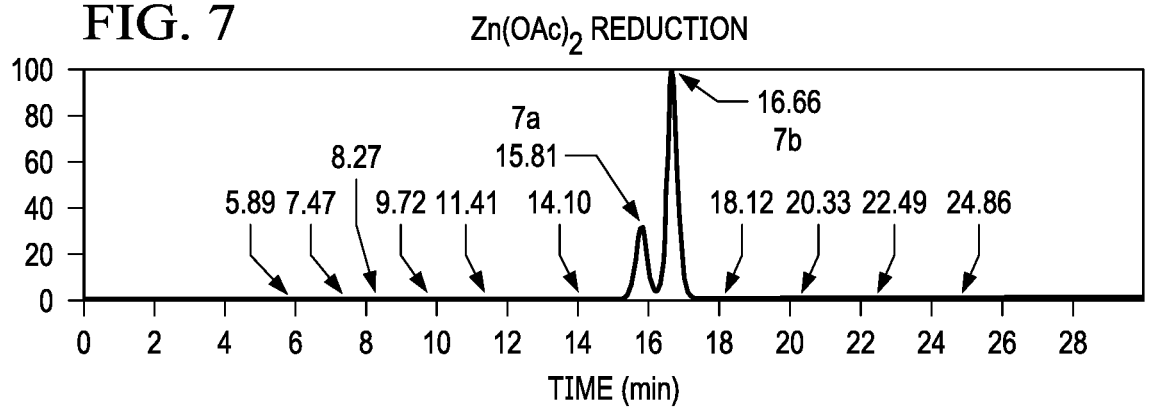
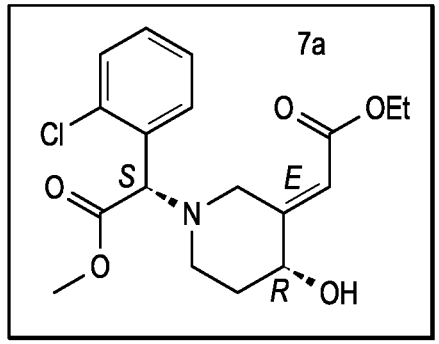
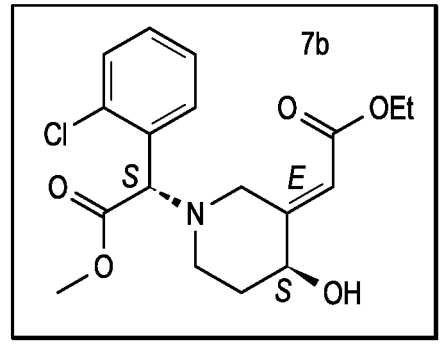

| Entry[a] | M(OAc)$_n$ | EQUIV. | 7a:7b[b] | Entry[c] | REDUCTANT | 7a:7b[b] |
|---|---|---|---|---|---|---|
| 1 | AgOAc | 2 | 1:1[d] | 10 | BH$_3$·DMS | 1:2 |
| 2 | Co(OAC)$_2$ | 2 | 1:1 | 11 | 9-BBN | 1:1 |
| 3 | Cu(OAC)$_2$ | 3 | 1:1[d] | 12 | CATECHOL BORANE | 1.2:1 |
| 4 | Hg(OAC)$_2$ | 3 | 2:1[d] | 13 | NaBH$_4$ | 1:1 |
| 5 | Ni(OAC)$_2$ | 3 | 1:1 | 14 | DIBAL-H | 1:1 |
| 6 | Pd(OAc)$_2$ | 2 | 1:1 | 15 | KBH$_4$ | 1:1 |
| 7 | Zn(OAC)$_2$ | 1 | 1:1.5 | 16 | SUPER HYDRIDE | 1:1 |
| 8 | Zn(OAC)$_2$ | 2 | 1:3 | 17 | NaBH$_3$CN | 1:1 |
| 9 | Zn(OAC)$_2$ | 3 | 1:2 | 18 | NaBH(OAc)$_3$ | 1.2:1[d] |

FIG. 8

CHEMICAL SYNTHESIS OF CLOPIDOGREL ACTIVE METABOLITES AND DISULFIDE CONJUGATE PRODRUGS

CROSS-REFERENCE TO RELATED APPLICATIONS

This application is related to and claims the benefit of priority of provisional U.S. Patent Application Ser. No. 62/906,644, filed Sep. 26, 2019, which is hereby incorporated by reference.

BACKGROUND OF THE INVENTION

1. Field of the Invention

The invention generally relates to the field of medicine, and in particular to the modulation of platelet aggregation.

2. Description of the Related Art

Since launched in 1997, antiplatelet prodrug clopidogrel (CPG) has been the mainstay medication for treating coronary heart diseases or preventing ischemic strokes. However, the prevalent treatment of CPG has been associated with a high level of clinical resistance, leading to FDA's black box warning of life-threatening recurrence of ischemic events.

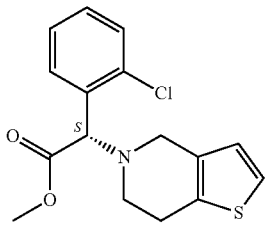

Referring now to FIG. 1, a schematic of the metabolic activation of CPG and metabolite derivatization is shown according to the prior art. CPG (M0, FIG. 1A) is inactive itself and undergoes extensive metabolism in patients. Only a very small portion of CPG is converted through a series of cytochrome P450 (CYP)-catalyzed thiophene degradation to form active metabolite H4 (FIG. 1A), an irreversible inhibitor of platelet aggregation. The inability to activate H4 due to various factors, including metabolic enzyme polymorphism or drug-drug interactions, has led to the observed irresponsiveness.

As illustrated, CPG are catalyzed by genetic polymorphic enzymes including CYP2C19 and CYP3A4. CYP, cytochrome P450; GSH, L-glutathione (reduced); GS-SG, L-glutathione disulfide (oxidized) (FIG. 1A). The thiophene-degradation substructure of M13 contains an exocyclic double bond and a stereogenic carbon center that bears a mercapto group, which can yield four diastereomers: H1 (3E, 4S), H2 (3E, 4R), H3 (3Z, 4S) and H4 (3Z, 4R) (FIG. 1A).

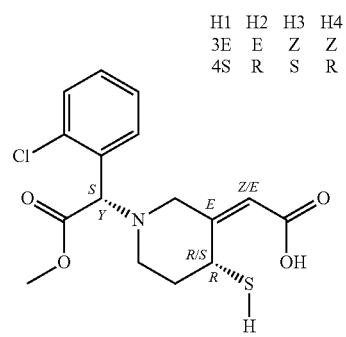

| | H1 | H2 | H3 | H4 |
|---|---|---|---|---|
| 3 | E | E | Z | Z |
| 4 | S | R | S | R |

Prepared from liver microsomal incubations of M0 or M2 in the presence of reductive thiols such as L-glutathione (GSH), all these isomers have been found to be chemically unstable and reactive, and their structures were established in the forms of stabilized derivatives.

Among the four diastereomers, only H3 and H4 have been detected as circulating metabolites in patients' plasma, and in vitro pharmacological studies have shown that H4 is active while H3 is not, which demonstrates that the configuration of the mercapto carbon is crucial to the antiplatelet activity. However, the (4R/S)-configuration of H3 and H4 have only been tentatively assigned, and the bioactive stereoisomer has yet to be experimentally elucidated.

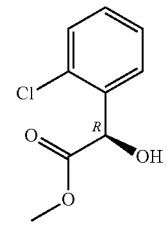

The circulating thiol metabolites are stabilized as phenacyl derivatives (H3/H4-MP) for clinical monitoring (FIG. 1B). Upon oral administration of CPG, H4 in patients' plasma is measured as its stabilized 3'-methoxyphenacyl derivative (H4MP), which has been the best marker of exposure and the parameter most closely correlated with the observed pharmacodynamic activities. These have established H4 as the putative active metabolite of CPG.

Direct administration of CPG active metabolite or its releasable derivatives may largely overcome the observed clinical resistances. Mixed disulfides of H3 and H4, including ClopNPT, prepared from human liver microsomal incubations of M2 in the presence of aryl thiols (FIG. 1C), have been shown to undergo quick reductive cleavage to release H3 and H4, suggesting that the mixed disulfide conjugates of active metabolites (e.g. H3/H4-NPT, ClopNPT) as drug candidates that require no bioactivation (FIG. 1C). In animal studies, ClopNPT has demonstrated potent antithrombotic effects along with other advantages such as fast onset and reduced bleeding risk. The preclinical studies of ClopNPT not only support the biochemical delineation of CPG irresponsiveness, but also further substantiate the need of synthesizing H4 for overcoming the antithrombotic resistances.

Unlike stable natural products with traceable biosynthesis, the instability and reactivity of the degradation structure of H4, as well as obstacles associated with its (Z)-exocyclic double bond, have posed significant challenges to organic synthesis. Separate syntheses of the S-phenacyl and S-acetyl protected H4, respectively, have recently been reported for clinical monitoring and analyte development. However, the reported routes are of overall low yields and are not stereoselective to the isomeric centers. For the potential release of H4, the reported derivatives need to undergo harsh deprotection procedures such as reflux in acid or treatment with strong base, which can decompose the labile metabolite.

SUMMARY

According to one or more embodiments of the present invention, a 10-step synthesis of the clopidogrel active metabolite, H4 and its analogy H2 is provided that mitigates the (Z)-conformation challenges through furnishing the (E)-intermediates followed by (E)-to-(Z) isomerization. The crucial (4R)-configuration is obtained from an unprecedented asymmetric reduction promoted by $Zn(OAc)_2$. The last step of (E)-to-(Z) isomerization is achieved through a reversible Michael reaction under biomimetic conditions. The synthetic H4 H2 and H4 mixed disulfides and H2 mixed disulfide has demonstrated stereospecific potency in mice and can be flexibly converted to its releasable forms including ClopNPT with established therapeutic enhancement. The synthetic access to H4 and H2 and their mixed disulfides abrogates the bioactivation dependence of CPG efficacy and can overcome the clinical resistances of its prevalent treatment. Chemical model studies have also revealed unconventional "on and off" reactivity of H4 and H2 against thiol reagents, which can both shed light to the antagonism mechanism of the G-protein-coupled $P2Y_{12}$ receptor and inspire chemical biology exploration of protein modification and regulation.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 6 is an analysis of non-selective ketone reduction using liquid chromatography with tandem mass spectrometry (LC-MS/MS) shown according to an illustrative example;

FIG. 7 is an analysis of selective ketone reduction using LC-MS/MS shown according to an illustrative example;

FIG. 8 is a table of reaction conditions for asymmetric ketone reduction shown according to an illustrative example;

DETAILED DESCRIPTION

Figure 1A:
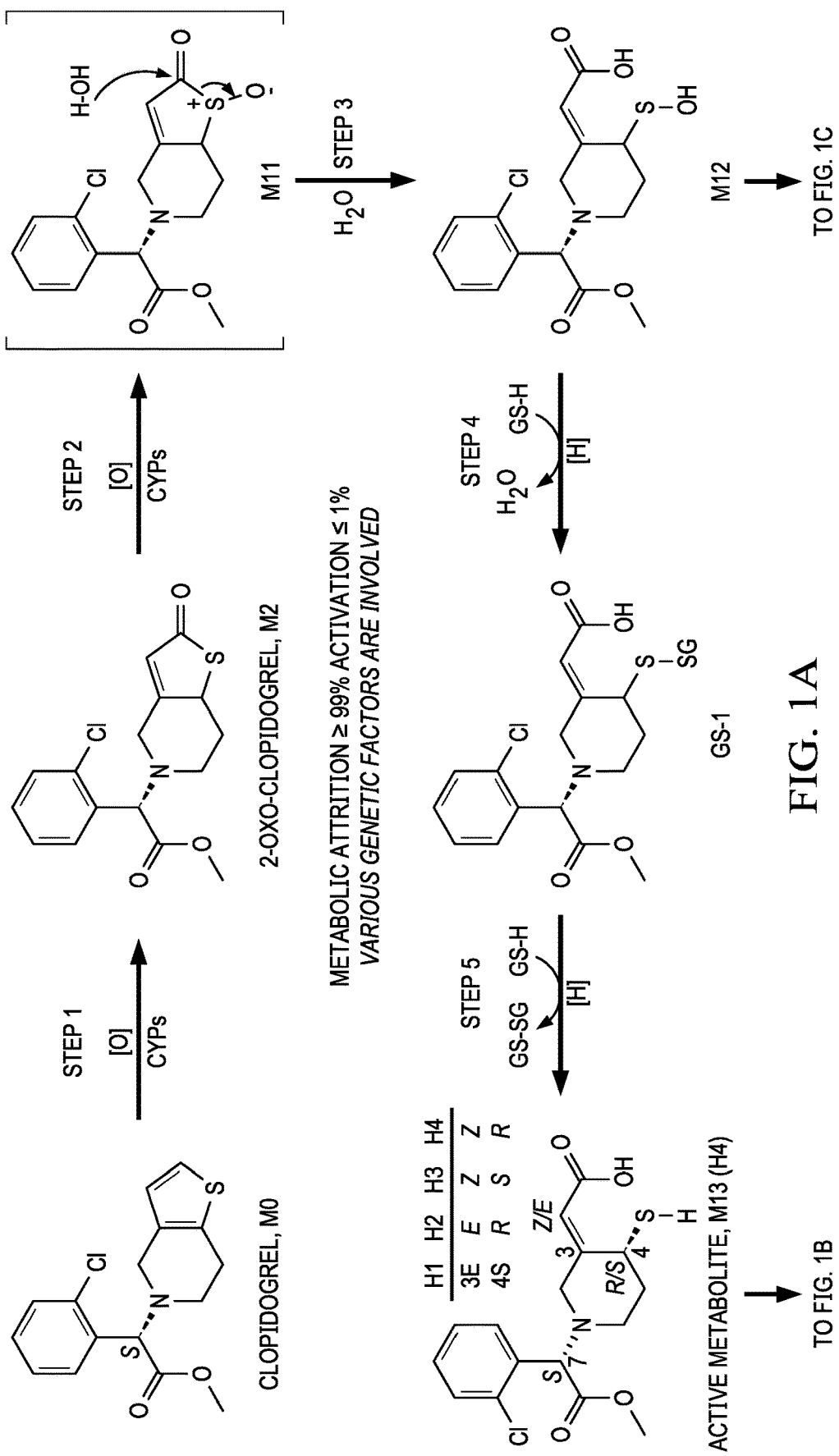
FIGS. 1A-C is a schematic of the metabolic activation of CPG and metabolite derivatization shown according to the prior art.

The illustrative embodiments recognize and take into account one or more different considerations. For example, prodrug clopidogrel (CPG) has been the mainstay antithrombotic agent since 1997. The active metabolite, H4, is a trivial product yielded from multistep metabolism catalyzed by genetic polymorphic enzymes, which underlines a high level of clinical resistance. The synthetic pursuit of H4 has long been hampered by not only its chemical instability and reactivity but also obstacles associated with its (Z)-exocyclic double bond.

On the basis of these considerations, the illustrative examples described herein provide a stereoselective and efficient synthesis of H4 under mild conditions. The illustrative examples provide a 10-step synthesis of H4 that mitigates the (Z)-conformation challenges through furnishing the (E)-intermediates followed by (E)-to-(Z) isomerization. The crucial (4R)-configuration is obtained from an unprecedented asymmetric reduction promoted by Zn(OAc)$_2$. The last step of (E)-to-(Z) isomerization is achieved through a reversible Michael reaction under biomimetic conditions. The synthetic H4 has demonstrated stereospecific potency in mice and can be flexibly converted to its releasable forms including ClopNPT with established therapeutic enhancement. The synthetic access to H4 abrogates the bioactivation dependence of CPG efficacy and can overcome the clinical resistances of its prevalent treatment. Chemical model studies have also revealed unconventional "on and off" reactivity of H4 against thiol reagents, which can both shed light to the antagonism mechanism of the G-protein-coupled $P2Y_{12}$ receptor and inspire chemical biology exploration of protein modification and regulation.

The illustrative embodiments described herein provide a method of synthesizing a clopidogrel metabolite is provided. The method includes forming a piperidone intermediate from a mandelate; performing an asymmetric ketone reduction of the piperidone intermediate; after performing the asymmetric ketone reduction, performing a mercapto installation to form the clopidogrel metabolite that includes a 4-carbon chiral center having an (R) configuration.

In an illustrative example, the piperidone intermediate can be formed by reacting methyl 2-chloro-D-mandelate with nosyl chloride and triethylamine to form a first intermediate; reacting the first intermediate with 4-piperidinol and potassium hydrogen carbonate to form a second intermediate; reacting the second intermediate with oxalyl chloride, dimethyl sulfoxide, and triethylamine to form a third intermediate; and forming the piperidone intermediate from the third intermediate. The third intermediate can be reacted with lithium diisopropylamide and ethyl glyoxalate to form the piperidone intermediate; alternatively, the third intermediate can be reacted with lithium diisopropylamide and ethyl glyoxalate to form a fourth intermediate that is reacted with p-toluenesulfonic acid to form the piperidone intermediate.

In an illustrative example, the asymmetric ketone reduction is performed by using a metal ion chelation to form a fifth intermediate, wherein the 4-carbon chiral center has an (S) configuration.

In an illustrative example, the clopidogrel metabolite can be formed by reacting the product of the asymmetric ketone reduction with methanesulfonyl chloride and diisopropylethylamine to form a sixth intermediate; reacting the sixth intermediate with triisopropylsilanethiol and sodium hydride to form a seventh intermediate; and reacting the seventh intermediate with hydrochloric acid to form the clopidogrel metabolite.

In an illustrative example, the clopidogrel metabolite is isomerized to the through a reversible Michael addition to form a second clopidogrel metabolite.

In an illustrative example, the clopidogrel metabolite can be converted to a stabilized mixed disulfide derivative.

The illustrative examples provided herein describe a stereoselective synthesis of H4 was accomplished in 10 steps. Without using additional chiral agents, the stereogenecity of the starting material, methyl 2-chloro-D-mandelate, is extended to obtain the crucial (R)-configuration of the mercapto carbon, which is promoted by $Zn(OAc)_2$. Based on the chemical reactivity of the exocyclic olefinic acetic acid, a reversible Michael reaction was conducted under biomimetic conditions to isomerize the (E)double bond to the desired (Z)-conformation at the final stage of synthesis. Both of the two stereoselective controls are achieved through facile but nontraditional approaches. The synthetic H4 has demonstrated stereospecific potency in vivo, and its bioactive (4R)-configuration is experimentally established. Flexible derivatization procedures have also been established to conveniently transform H4 to its stable and releasable forms for drug development.

The synthetic access to H4 abrogates the bioactivation dependence of CPG efficacy and can overcome the clinical resistances of its prevalent treatment. With the growing evidence of $P2Y_{12}R$ involvement in many essential pathological processes, synthetic H4 in its suitable derivatization forms might be repurposed to treat other diseases such as cancer metastasis, neuronal disorder, or autoimmune encephalomyelitis.

EXAMPLES

Retrosynthetic Analysis

Figure 2:
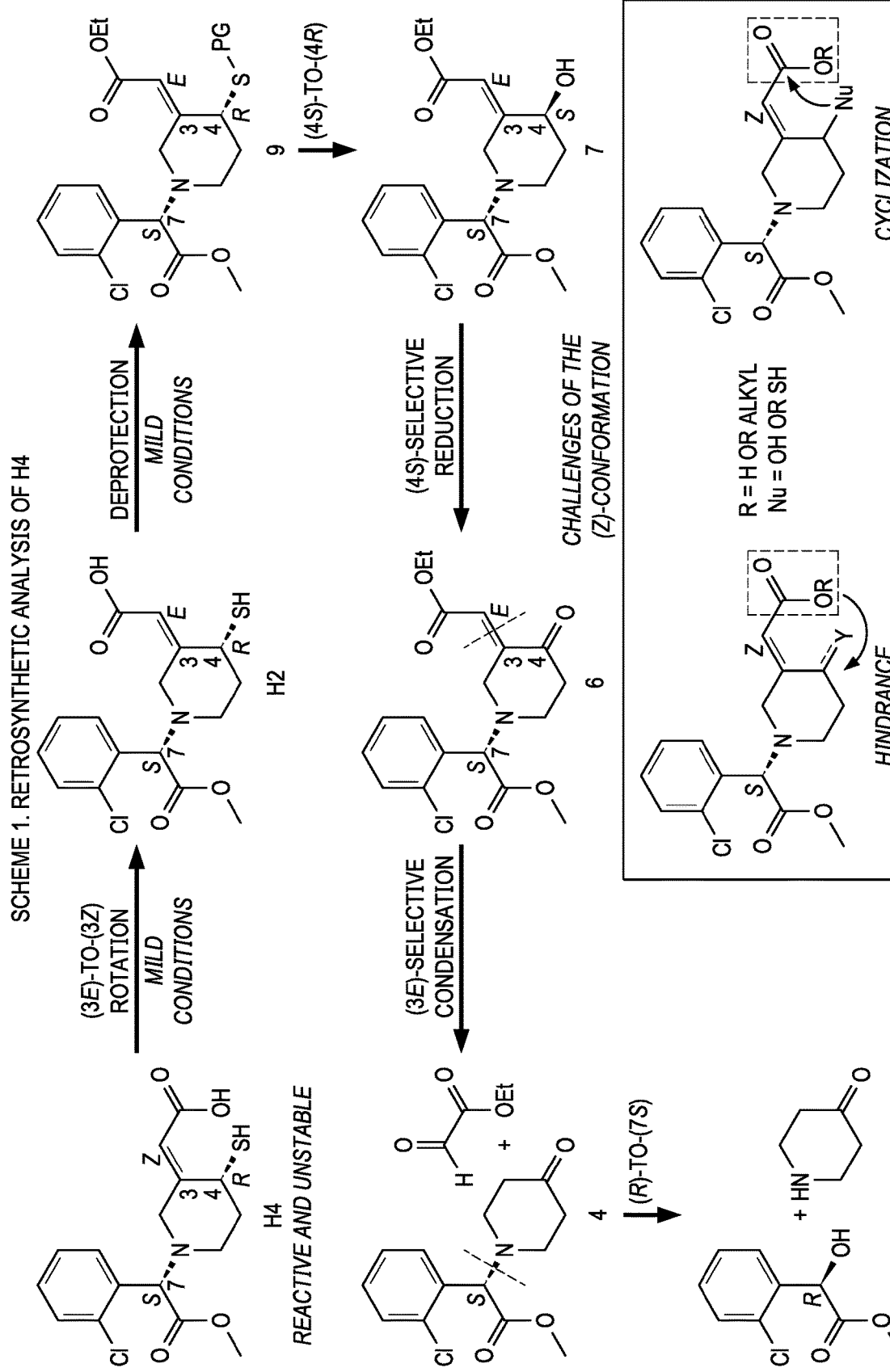
FIG. 2 is a schematic of a retrosynthetic analysis of a CPG active metabolite shown according to an illustrative example.

Referring now to FIG. 2, a schematic of a retrosynthetic analysis of a CPG active metabolite is shown according to an illustrative example. The key consideration is the crucial (4R)-configuration of the mercapto carbon. To achieve it, a piperidone intermediate (4) was employed for an asymmetric ketone reduction followed by an SN2 reaction of mercapto installation. Piperidone 4 can be prepared from methyl 2-chloro-D-mandelate (1).

The ketone functionality in 4 can also allow an installation of the α-olefinic acetic acid fragment through a condensation reaction with glyoxylate. However, the condensation is expected to selectively yield the (3E)-product 6. Although the (E)-conformation is not desired, it keeps the carboxylate away and makes the ketone functionality in 6 less hindered for selective reduction and subsequent transformation, which have proved to be challenging with the (Z)-conformation.

Previous studies have also shown that the (Z)-double bond can foster intramolecular cyclization including the recovery of thiolactone intermediate (M2) from H3 and H4. To mitigate the challenges associated with the (Z)-conformation the illustrative examples first furnish the (3E)-intermediates including obtaining the key (4R)-configuration and isomerize the double bond to the desired (3Z)-conformation at a late stage of the synthesis.

Synthesis of Piperidone Intermediate 6.

Figure 3:
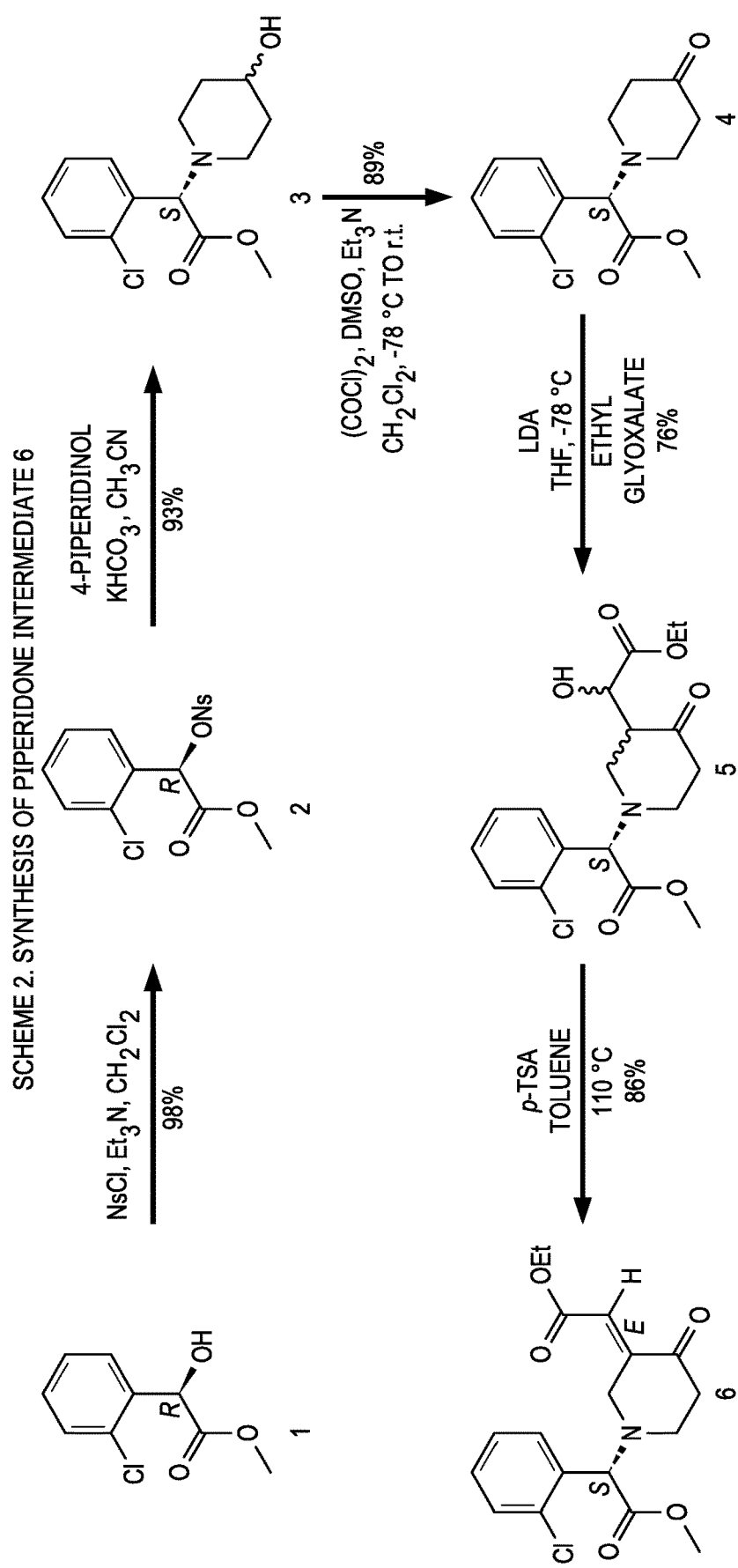
FIG. 3 is a schematic of the synthesis of a piperidone intermediate shown according to an illustrative example.

Referring now to FIG. 3, a schematic of the synthesis of a piperidone intermediate is shown according to an illustrative example. The synthesis is commenced with the preparation of (6) containing an (E)double bond. As shown, mandelate (1) was first converted to its nosylate (2) in 98% yield.

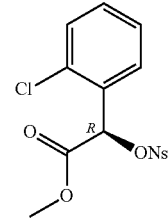

Piperidinol (4) was employed to react with 2 to invert the mandelate chiral center and overcoming the poor nucleophilicity of the piperidone N-atom to afford 3 in 93% yield.

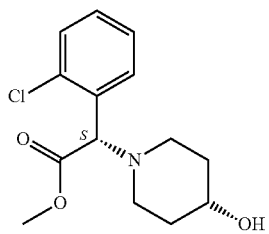

The resulting alcohol 3 then underwent a Swern oxidation to form ketone 4 in 89% yield.

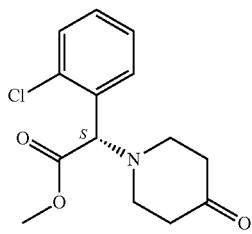

In an illustrative example, 4 first underwent a pyrrolidine-assisted direct condensation with ethyl glyoxylate in toluene, and 6 was obtained as the only product in 25% yield.

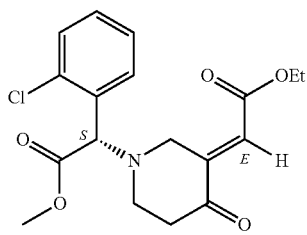

In an alternative example, 4 underwent an alternative reaction with LDA followed by addition of ethyl glyoxylate to form (5) in 76% yield.

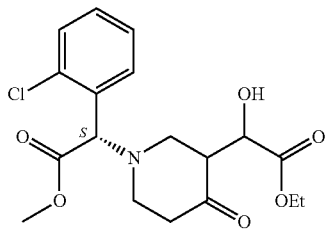

The alcohol intermediate 5 was dehydrated through either refluxing in toluene at 110° C. with p-TSA or stirring at 0° C. in the presence of $POCl_3$ and pyridine; the former condition offers higher yield (86%) than the latter (74%), and in both cases, only (E)-condensation product 6 was obtained.

Asymmetric Reduction of Ketone 6.

As elaborated in FIG. 2, to obtain the crucial (4R)-configuration in H4, the prochiral ketone functionality in 6 needs to undergo an asymmetric reduction to form (7) with a (4S)-configuration, which can be inverted to the (4R)-configuration by an SN2 mercapto substitution.

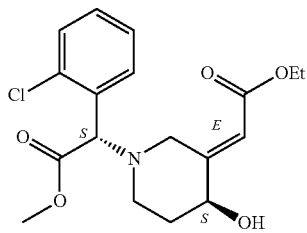

Figure 4:
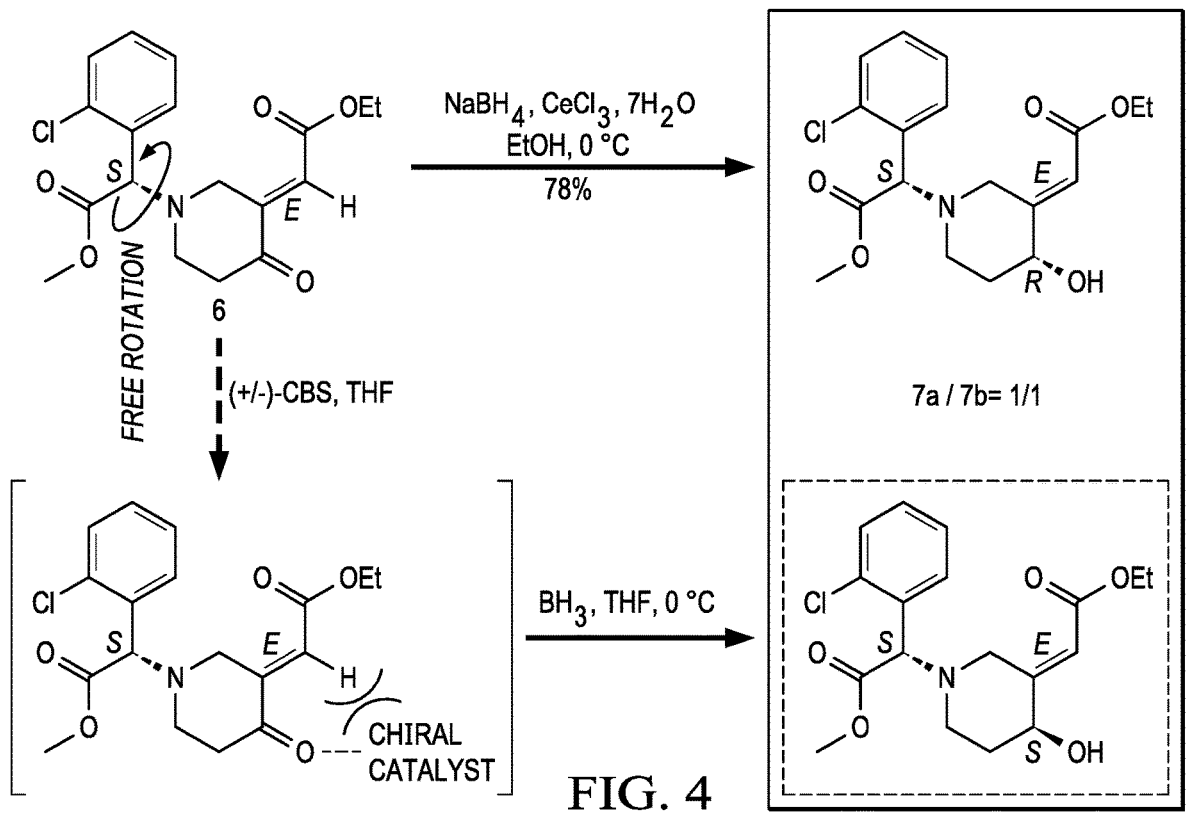
FIG. 4 is a schematic of an asymmetric reduction of a piperidone ketone shown according to an illustrative example.

The (3E)-double bond in 6 keeps the ketone functionality relatively open. Although there is an (S)-carbon in the mandelate moiety, it is not close enough to the ketone functionality to cast a stereomeric impact. The free rotation of the C—N single bond of this stereogenic center makes the two prochiral ketone faces nonselective. To obtain the chemical reference, 6 first underwent a nonselective Luche reduction (FIG. 4). The resulting 7 shows a pair of diastereomers at equal amounts (7a:7b=1:1) under LC-MS/MS analysis (FIG. 6). After these, 6 was treated with borane in THF in the presence of (+)-CBS or (−)-CBS for asymmetric reduction. No selectivity was observed, suggesting that the ketone functionality in 6 cannot effectively coordinate with the chiral catalyst, which might be due to low affinity of the conjugated ketone or hindrance from the neighboring (E)-olefin-H.

Figure 5:
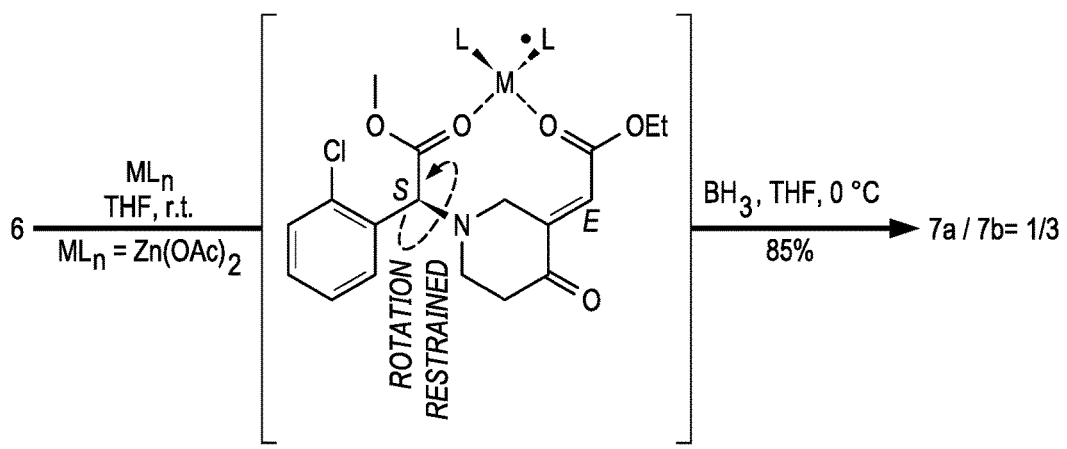
FIG. 5 is a conceptual design of chirality extension through metal ion chelation shown according to an illustrative example.

Free rotation of the C—N single bond of this stereogenic center (S)-carbon in the mandelate moiety makes the two prochiral ketone faces nonselective. Restraining free rotation of this single bond enables the two prochiral faces to be differentiated for asymmetric reduction. As this single bond rotates, the mandelate methyl ester can get close to the (E)-olefinic ethyl acetate (4-6 Å); these two esters are be able to chelate to a transition metal ion, which in return can restrain the C—N bond rotation, as illustrated in FIG. 5.

Metal ion chelation was formulated to exploit the internal stereogenicity of 6 for the desired asymmetric ketone reduction. In the initial screening, various acetates of transition metals were stirred with 6 in THF at room temperature for 1 hour before the addition of borane at 0° C. As shown in FIG. 6, $Zn(OAc)_2$ promoted asymmetric reduction among the tested salts.

The conditions of this $Zn^{2+}$-promoted asymmetric ketone reduction were optimized, as shown in FIG. 6. An 85% yield with a diastereomeric ratio of 7a:7b=1:3 was obtained. The advantage of this asymmetric reduction is that no external chiral reagent is used while the addition of $Zn^{2+}$ extends the remote chirality of the molecule and enables the asymmetric reaction.

Ketone groups are known to directly participate in metal ion chelation to promote selective reduction of itself. However, since the planar ketone functionality in 6 cannot participate in metal ion chelation together with the chiral mandelate, the coordination of the two remote esters creates the selectivity.

Mercapto Installation and Double Bond Isomerization.

Figure 9:
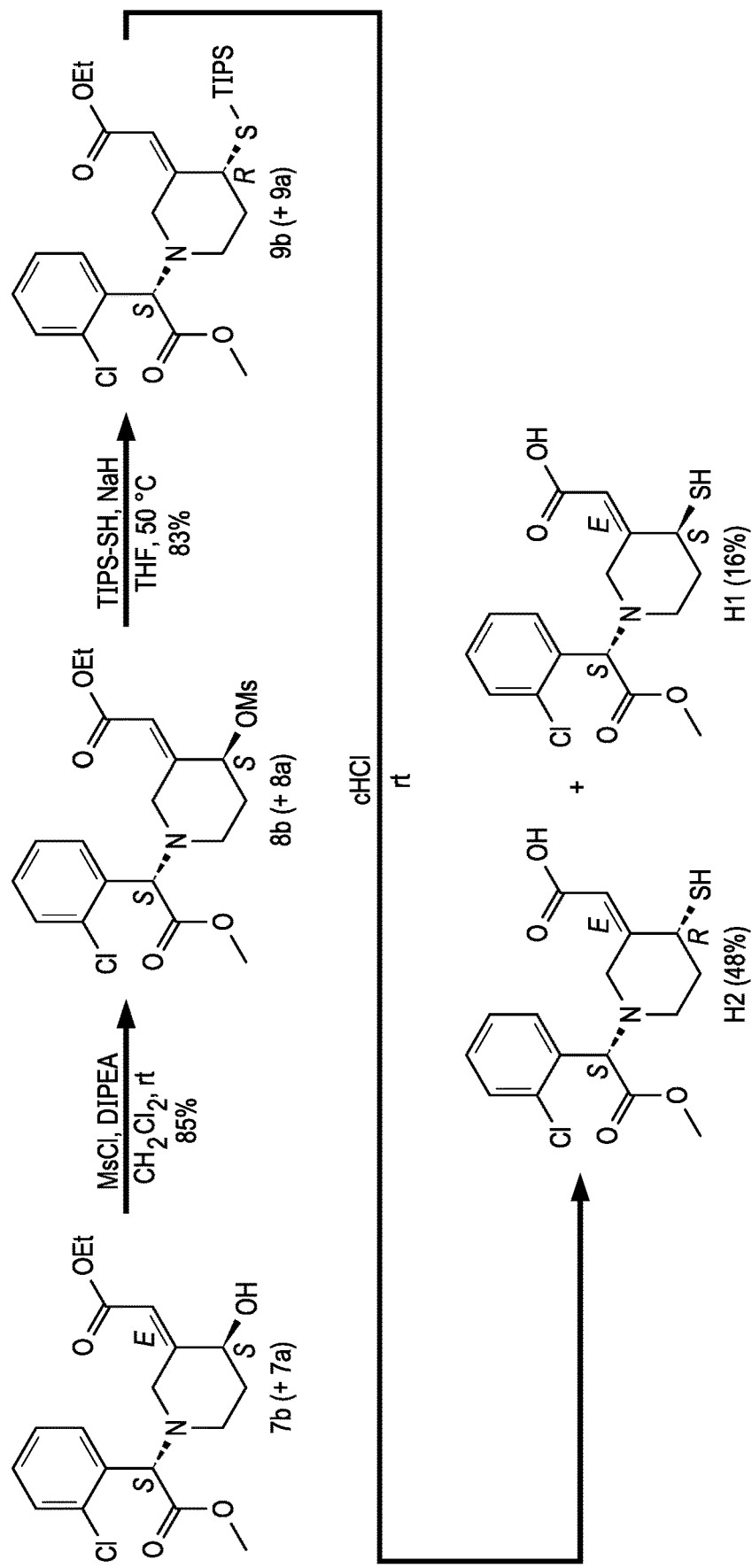
FIG. 9 is a schematic of mercapto installation and double bond isomerization shown according to an illustrative example.

Referring now to FIG. 9, a schematic of mercapto installation and double bond isomerization is shown according to an illustrative example Without separation, the diastereomeric mixture of 7 (7a:7b=1:3) was converted to mesylate 8 in 85% yield.

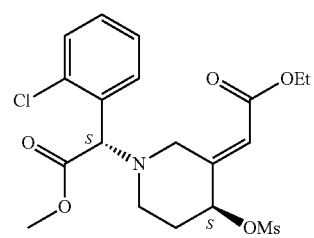

An SN2 substitution reaction with TIPS-SH was employed to afford the protected mercapto derivative 9 in 83% yield. The selectively obtained (4S)-configuration is inverted to the crucial (4R)-configuration. TIPS can be deprotected under mild acidic condition while deprotection of the S-acetyl group requires strong base, which might decompose the labile metabolites. Therefore, TIPS-SH is preferred over the more common sodium thioacetate for the mercapto installation.

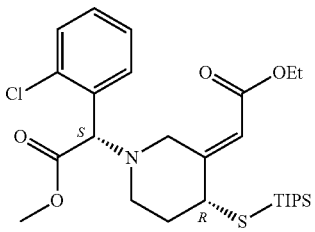

Using 37% hydrochloric acid at room temperature, 9 underwent quick deprotection of the TIPS group followed by selective ethyl ester hydrolysis of the E-olefinic acetate to afford H1 and H2, in 16% and 48% yield, respectively. The obtained H2 is the (E)-isomer of H4.

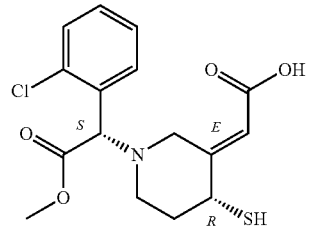

Double Bond Isomerization

Biosynthesized H2 has been shown to be similarly potent as H4 against $P2Y_{12}R$ in vitro, although it is not detected in patients. To isomerize the double bond in H2 to the desired (Z)-conformation under mild conditions, a reversible Michael reaction was considered. The exocyclic olefinic acetic acid moiety in H2 is a Michael reaction acceptor but the cyclic β-carbon might make the addition product unstable for quick elimination, which will lead to isomerization of the exocyclic double bond. Liver microsomal studies of CPG have shown that the bioactivated H3 and H4 [(Z)-double bond] undergo isomerization to H1 and H2 [(E)-double bond], respectively, in the presence of GSH. This double bond isomerization is a result of reversible Michael reaction. On the basis of these analyses, the final conversion of H2 to H4 was conducted in potassium phosphate buffer (KPi, pH 7.4) at 37° C. using GSH as the nucleophile for the reversible Michael reaction.

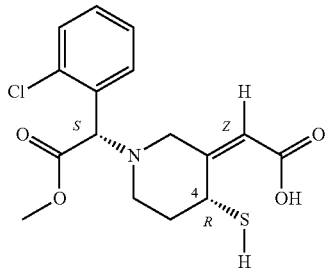

Figure 10:
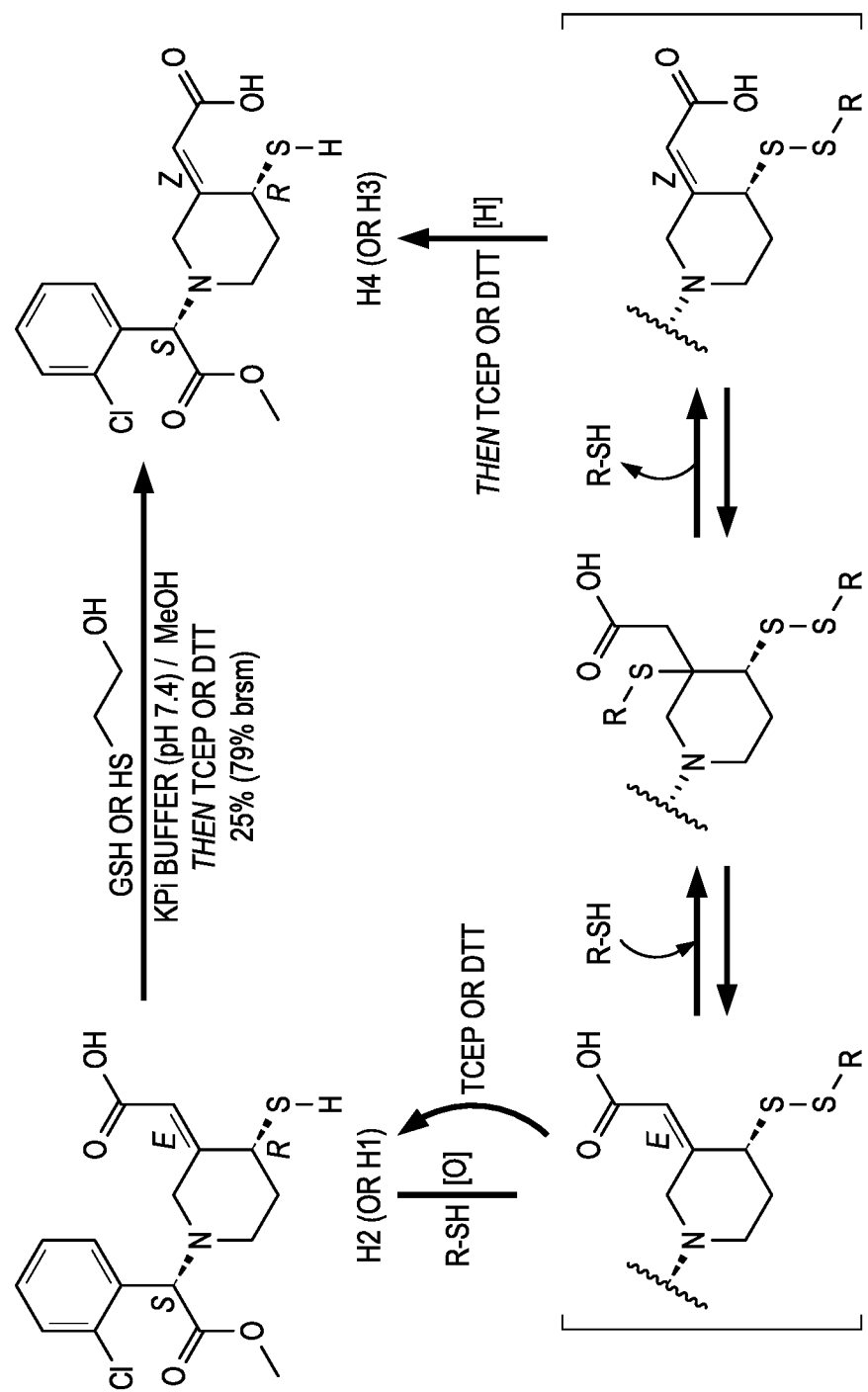
FIG. 10 is a schematic of the exocyclic double bond isomerization through a reversible Michael addition shown according to an illustrative example.
Figure 11:
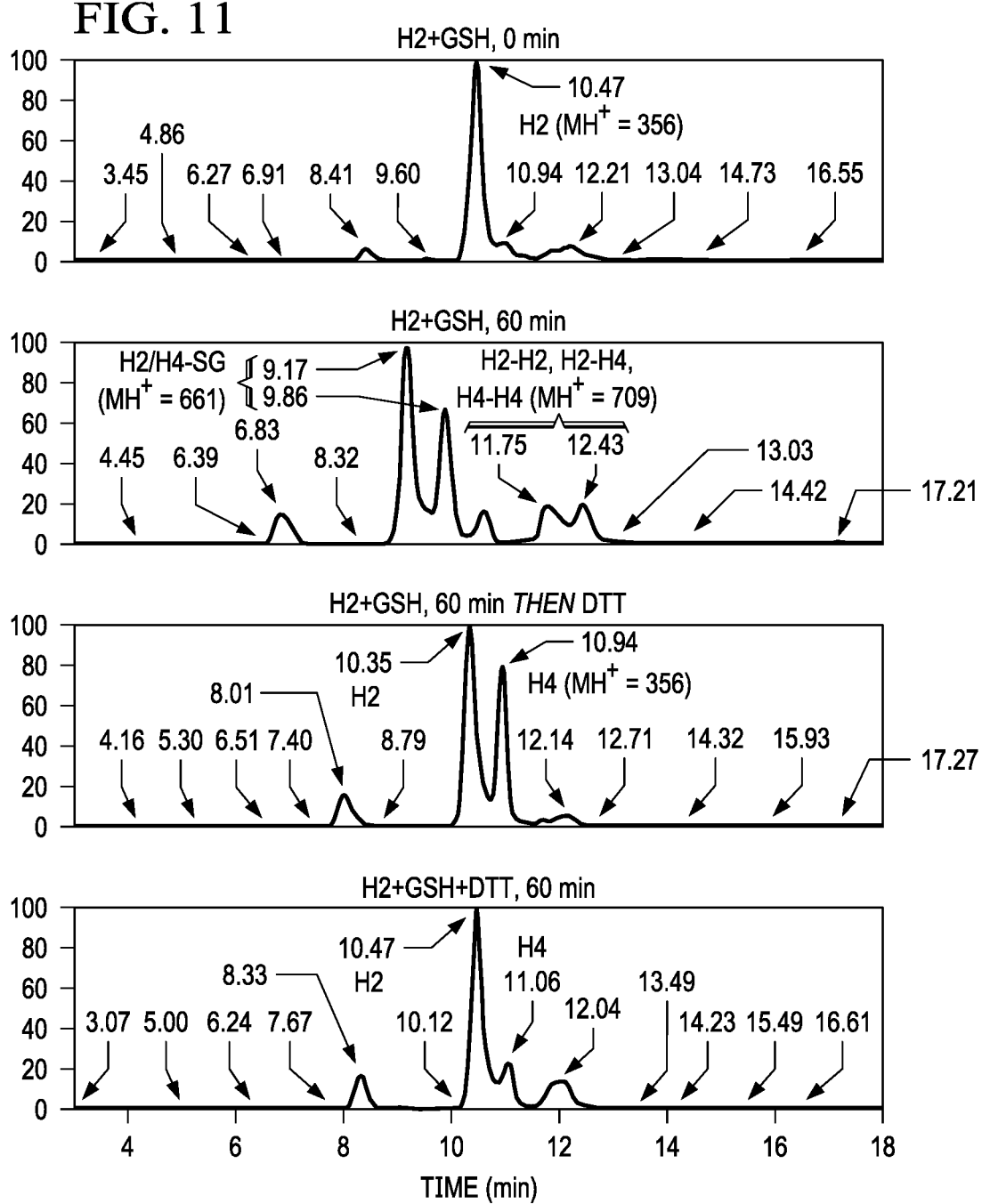
FIG. 11 is an analysis of the H2 metabolite double bond isomerization to the H4 metabolite using LC-MS/MS shown according to an illustrative example.

A major consideration of developing a biomimetic procedure for the final double bond isomerization is to ensure the stabilities of the labile metabolites. Upon incubation with GSH in KPi buffer (pH 7.4), H2 was found to undergo the desired double bond isomerization, as depicted in FIG. 10. LC-MS/MS studies of FIG. 11 show that H2 and H4 exist as disulfides with GSH or with themselves in the reaction mixture, and addition of bioreductants such as DL-dithiothreitol (DTT) or tris(2-carboxyethyl)phosphine (TCEP) can quickly cleave the disulfides to yield the metabolites. Inclusion of DTT or TCEP in the incubation was found to largely inhibit the isomerization, suggesting that the reversible Michael reaction takes place after the metabolites form disulfides.

The conditions of this biomimetic reaction were subsequently optimized, and the double bond isomerization was found to reach equilibrium after 2 hours with a ratio of H2:H4=1:1 (not shown). In scaled-up preparations, methanol and KPi buffer (pH 7.4) (1/1, v/v) was used as solvent to ensure the solubility of H2 and H4, and hydrophilic GSH was replaced by 2-mercaptoethanol (ME). H4 was obtained in isolated yield of 25% (79% brsm). Although this (E)-to-(Z) double bond isomerization is not highly efficient due to the nature of the equilibrium, the two isomers can be conveniently separated by liquid chromatography, and the recovered H2 can be converted to H4 by using this facile biomimetic protocol.

Figure 12:
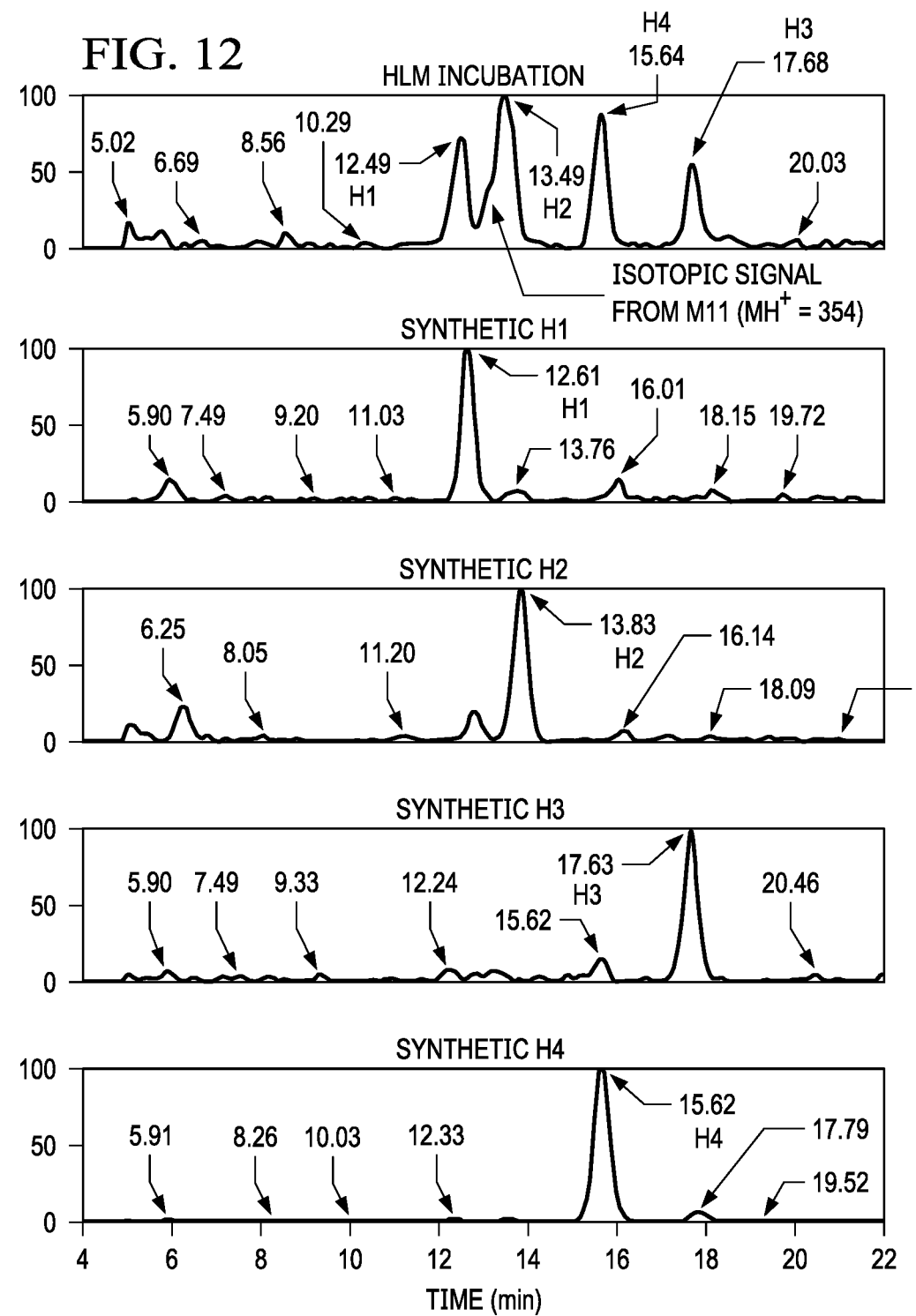
FIG. 12 is a comparison of metabolites from liver microsomal incubation and chemical synthesis using LC-MS/MS shown according to an illustrative example.

Similar to the preparation of H4 from H2, H3 was obtained from H1 (FIG. 10). LC-MS/MS studies of FIG. 12 confirmed all the synthetic metabolites are identical to those generated in human liver microsomal incubations. On the one hand, the successful preparation of these delicate degradation metabolites are attributable to the use of mild reaction conditions; on the other hand, these procedures have demonstrated that the metabolites can be stable in neutral or acidic solutions at up to 37° C.

Figure 1C:
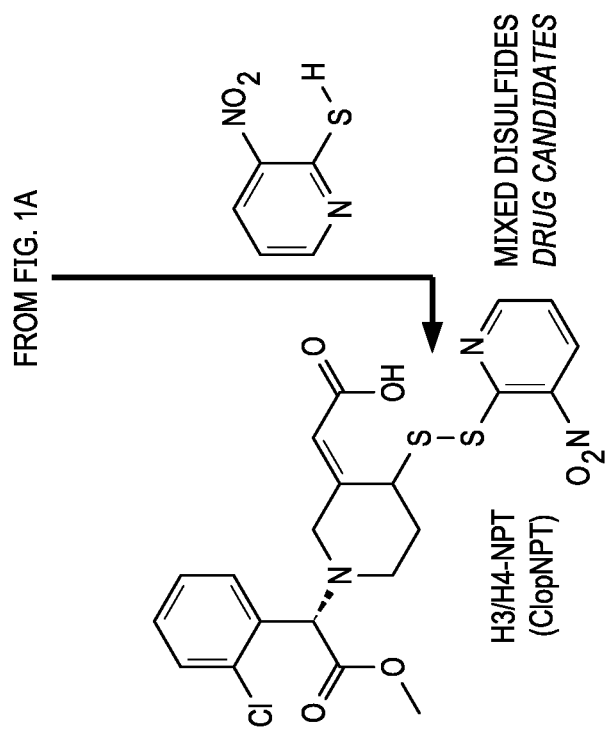
Figure 1B:
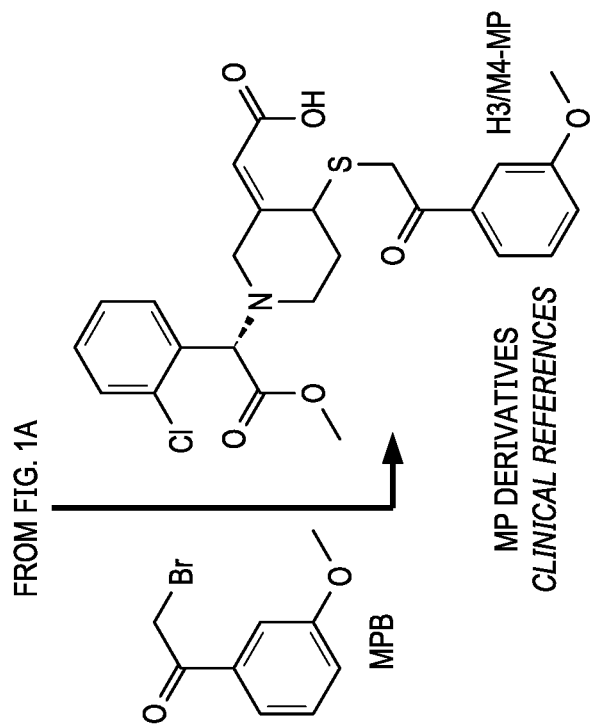

Chemical Derivatization of H4 to Stabilized Forms for Clinical Monitoring or Drug Development In clinic, the treatment of CPG relies on H4 plasma monitoring for managing the antithrombotic efficacy and the adverse events of bleeding. Upon oral administration, plasma samples of patients are treated with derivatization reagent MP-Br, and the circulating H4, together with its inactive diastereomer H3, are monitored by LC-MS/MS in the forms of their stabilized phenacyl derivatives, H4-MP and H3-MP, respectively (FIG. 1B).

Accurate clinical monitoring requires pure reference compound, and previously reported liver microsomal preparation or synthetic route proves to be inefficient. As a result, the commercial references are only available at daunting prices.

Figure 13:
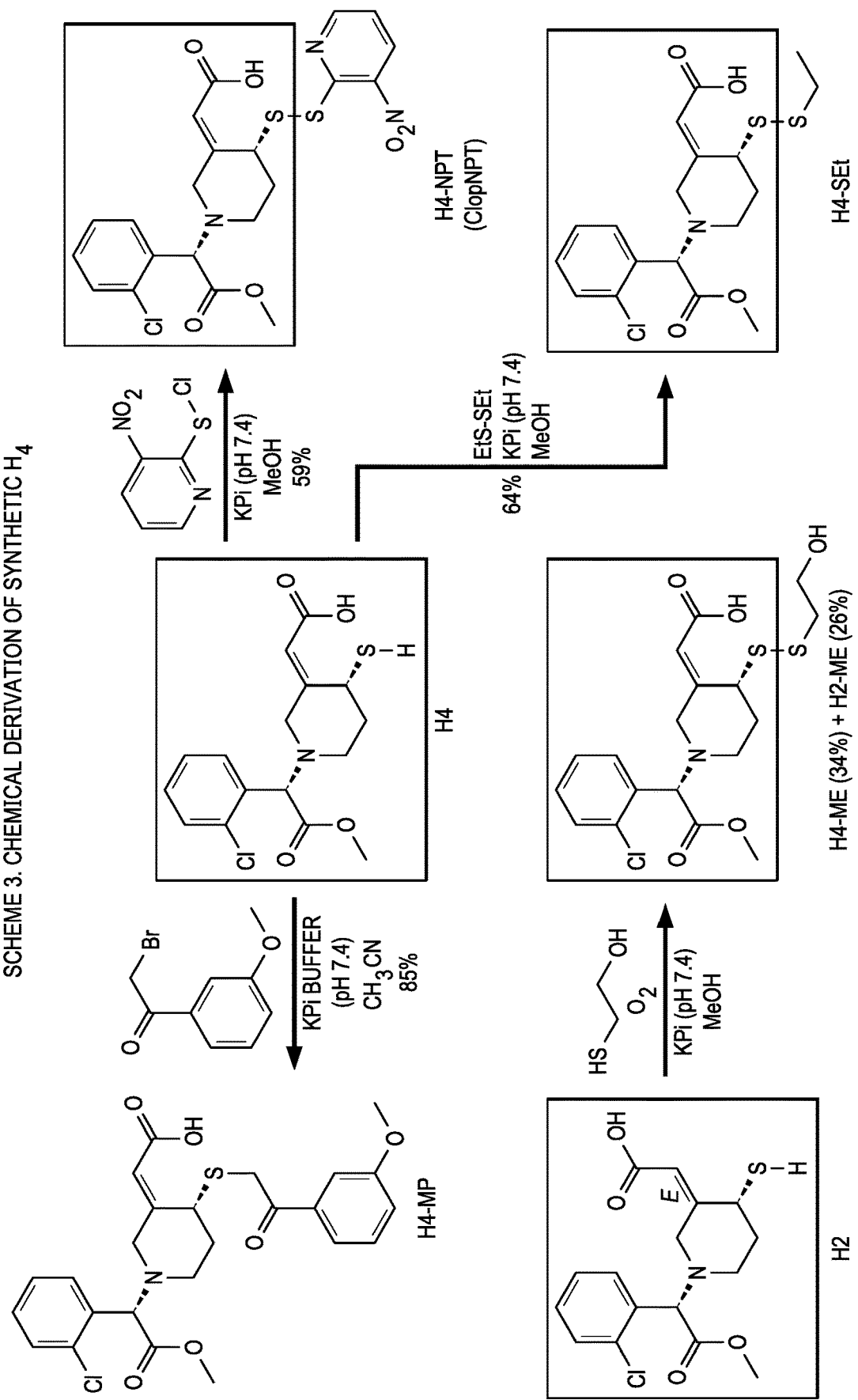
FIG. 13 is a schematic of a chemical derivation of synthetic H4 metabolite shown according to an illustrative example.

As illustrated in FIG. 13, the active metabolites obtained from the embodiments described herein can be conveniently converted to the phenacyl references through adopting the clinical derivatization procedures followed by facile purification. H4-MP and H3-MP were obtained in 85% yield and 80% yield, respectively. The synthetic derivatives have been confirmed by both LC-MS and NMR studies to be identical to the reported references (not shown). The improved synthetic access to H4-MP and H3-MP can aid reliable clinical monitoring on individual's response to CPG, which can lead to the optimization of existing dosing regimens or the design of personalized treatment for overcoming the CPG drawbacks.

The synthetic H4 can also be conveniently converted to its stabilized and releasable forms of mixed disulfides including prodrug candidate ClopNPT. Originally obtained as a mixture of H3-NPT and H4-NPT from human liver microsomal incubations, as shown in FIG. 1C, ClopNPT is a facile prodrug that can undergo quick reductive disulfide cleavage to release the active metabolite. In the biosynthetic preparation, only inert aryl thiols can be used to trap the active metabolite precursor of sulfenic acid (M12) to yield the mixed disulfides. Alkyl thiols including GSH can over react with the mixed disulfide to form the fully reduced metabolite (FIG. 1A).

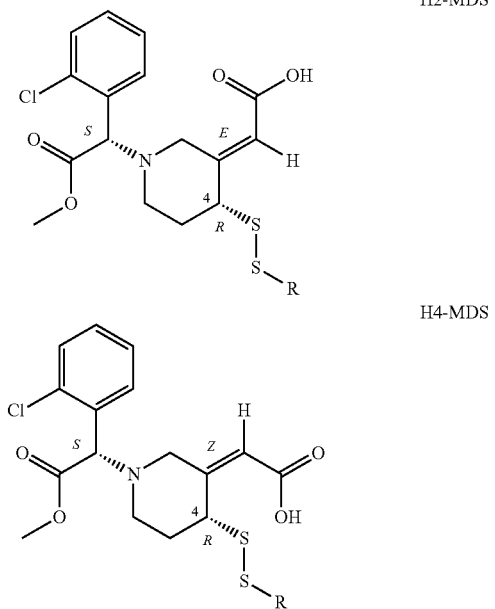

In one or more illustrative examples, the R chemical moiety can be, for example, but not limited to, one or more of alkyl, alkenyl, cycloalkyl, alkynyl, arylalkyl, aryl, heteroaryl, heterocycle, and cycloalkyl. In one or more illustrative examples, the alkyl, alkenyl, cycloalkyl, alkynyl, arylalkyl, aryl, heteroaryl, heterocycle, and cycloalkyl can be substituted or unsubstituted with one or more suitable substituents.

In one or more illustrative examples, the R chemical moiety can itself be the H2 metabolite, the H4 metabolite, or combinations thereof. In these illustrative examples, the metabolites can take the form of a homo-conjugate, such as H2-H2 and H4-H4; the metabolites can take the form of the hetero-conjugate H2-H4.

In these one or more illustrative examples, the R chemical moiety will render the resulting compound, H2-MDS or H4-MDS, capable of yielding antiplatelet agent H2 through reductive disulfide cleavage upon reaction with endogenous glutathione (GSH), cysteine, homocysteine or other bioreductive agents.

Referring now to FIG. 13, a schematic of a chemical derivation of synthetic H4 metabolite is shown according to an illustrative example. For chemical preparation of Clo-pNPT, synthetic H4 was dissolved in a mixture solvent of KPi buffer (pH 7.4) and methanol (1/1, v/v), and the sulfenyl chloride form of NPT was added to react with the sulfhydryl group of H4 to afford the desired conjugate in 59% yield.

Figure 15:
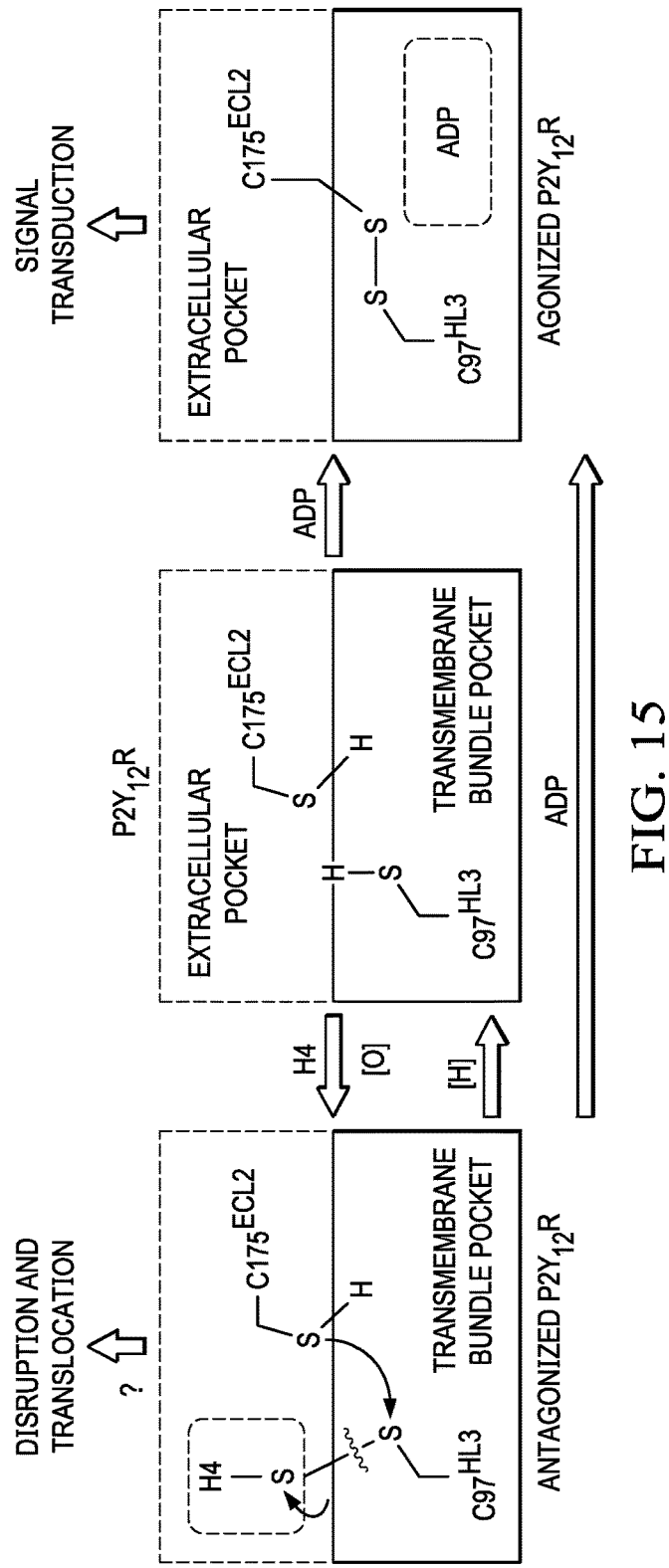
FIG. 15 are proposed pathways of $P2Y_{12}R$ antagonism by ADP and H4, shown according to an illustrative example.
Figure 16:
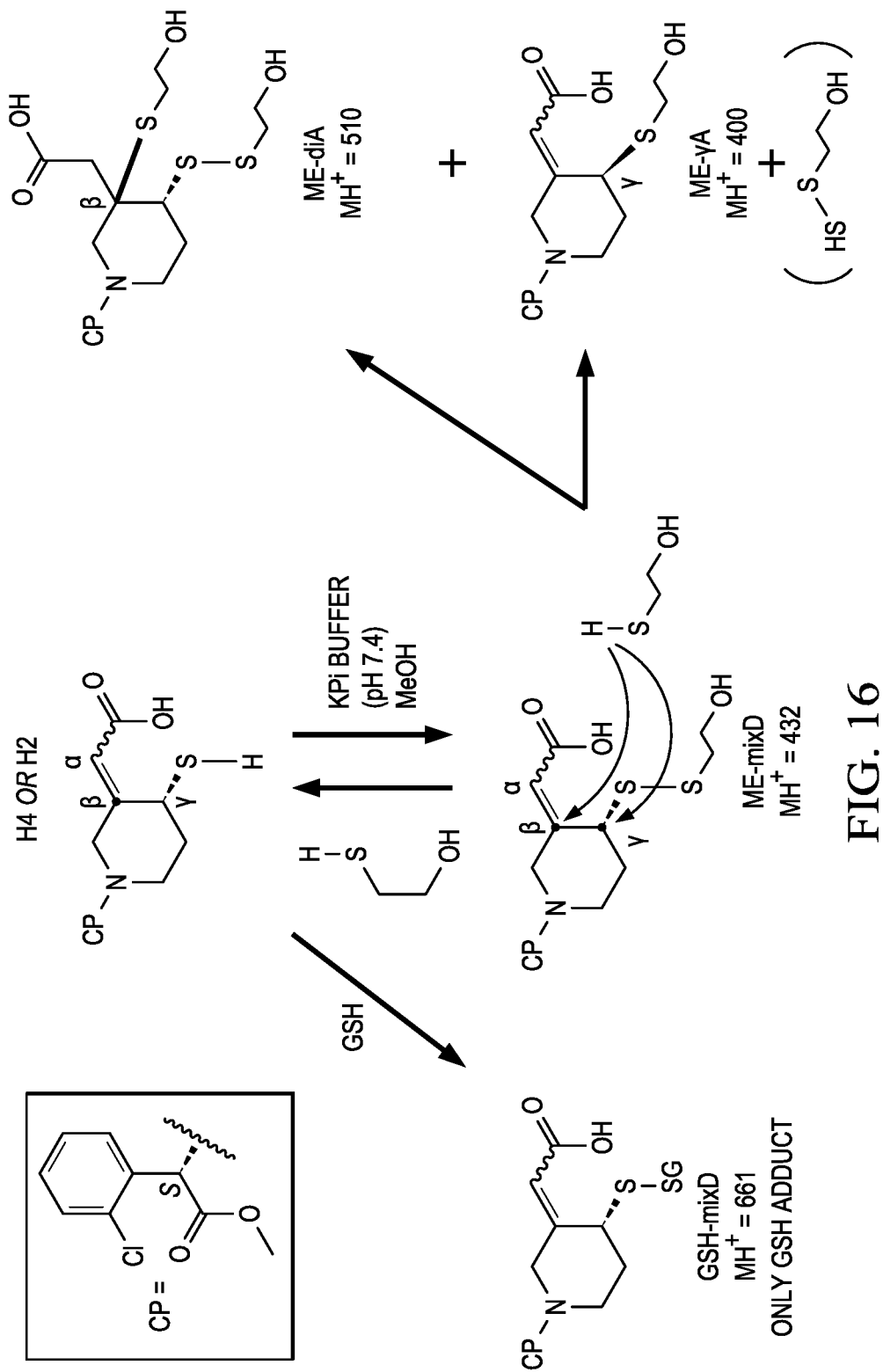
FIG. 16 is a schematic of chemical model studies of active metabolites with GSH and ME, shown according to an illustrative example.
Figure 17:
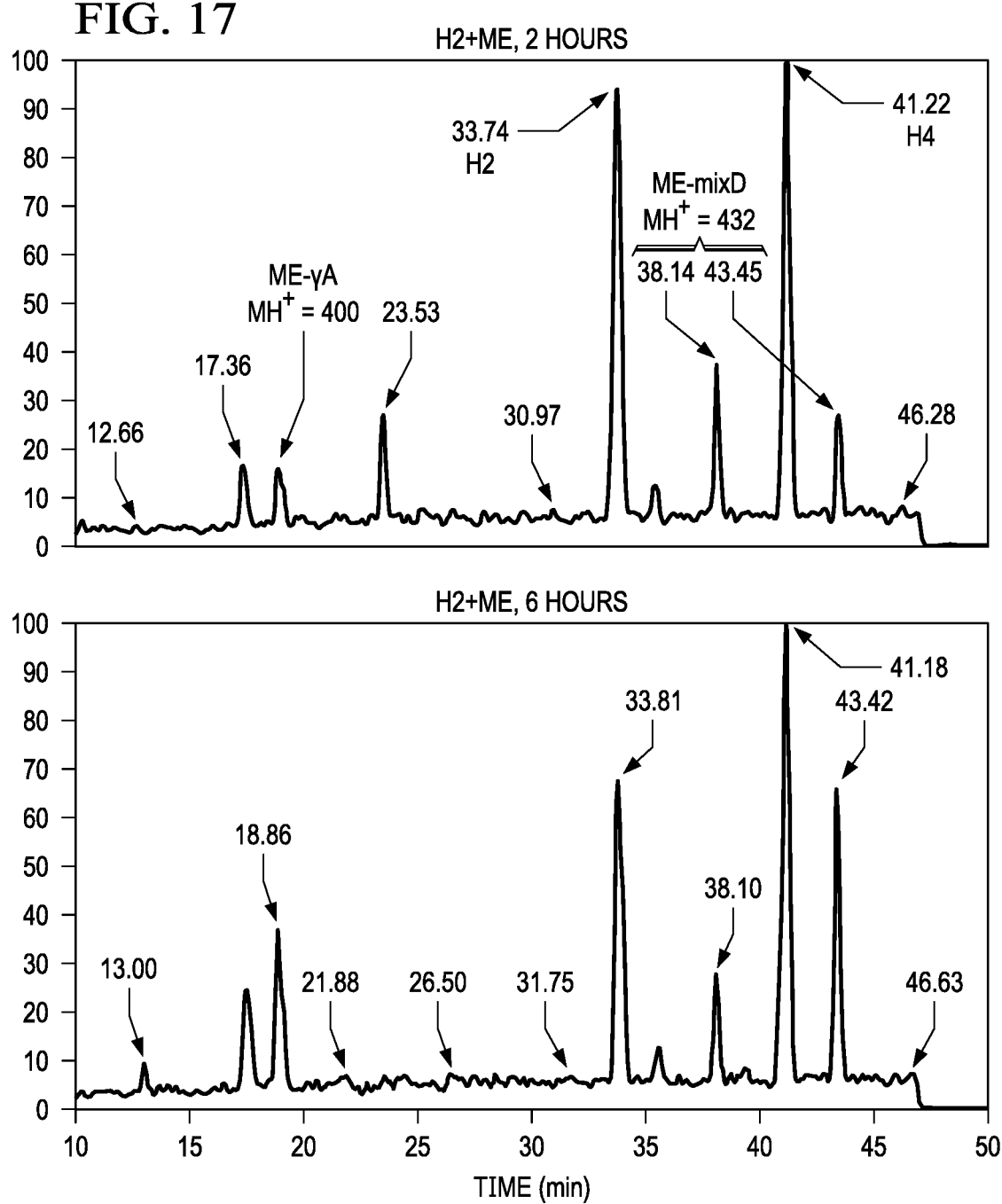
FIG. 17 is a comparison the chemical model studies of FIG. 16 using LC-MS/MS shown according to an illustrative example.

The individually synthesized H4-NPT and H3-NPT have shown to be identical to the diastereomeric mixture prepared according to the reported human liver microsomal procedures. To expand the scope of the mixed disulfide synthesis, a representative alkyl disulfides, diethyl disulfide, was used to replace the aryl sulfenyl chloride in the same reaction, and the corresponding ethyl disulfide of H4 was conveniently obtained in 64% yield. In addition to the direct derivatization of H4, mixed disulfides of H2 and H4 are the double bond isomerization intermediates of H2 conversion to H4, as shown in FIGS. 15 and 16, suggesting that the mixed disulfides of H4 can be obtained directly from the synthetic precursor, H2, through reaction with free thiols.

To test whether H4 can be obtained directly from the synthetic precursor, H2 was stirred with excessive ME under the biomimetic conditions of double bond isomerization. Mixed disulfide of H4-ME was obtained together with H2-ME, in 34% and 26% yield, respectively.

These chemical syntheses of H4 mixed disulfides can not only overcome the aforementioned limitations associated with biosynthesis, but more importantly, expand the choices of conjugates from limited aryl thiols to large pools of aryl or alkyl moieties in the forms of sulfenyl chloride, symmetric disulfides or free thiols. The flexible preparation procedure can channel drug development campaigns of screening and tuning the physiochemical properties, disulfide cleavage rate as well as the toxicity profiles of the cosulfide moieties in discovering the next generation antiplatelet agents.

In vivo Analysis

In vivo studies of synthetic metabolites and mechanistic exploration of protein antagonism through model thiol reactions. Although CPG has been used in clinic for over twenty years, the putative active metabolite, H4, including its tentatively assigned (4R)-configuration, has not been confirmed in vivo.

Figure 14:
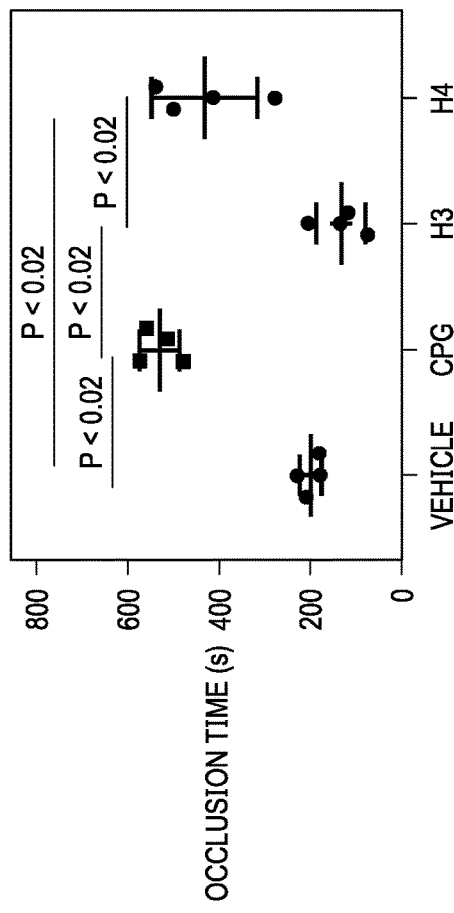
FIG. 14 are anti-thrombosis tests of synthetic H3 and H4 metabolites in mice, shown according to an illustrative example.

Referring now to FIGS. 14-18, In vivo antiplatelet test of synthetic H3 and H4 in a FeCl$_3$ carotid artery injury-induced thrombosis mouse model. As shown in FIG. 14, upon tail vein administration of 1 mg/kg, synthetic H4 was found to significantly prolong the occlusion time of thrombosis while synthetic H3 was found to be ineffective, as compared to the negative control of vehicle and the positive control of CPG.

The results of FIG. 14 are consistent with preciously reported in vitro studies and can serve as the first in vivo data that directly supports H4 to be the active metabolite of CPG. From these studies, the tentatively assigned (4R)-configuration of H4 is also experimentally established. It is important to note that the occlusion time deviation of the H4 group is considerably higher than that of the CPG group, which suggests that the polar and reactive structure of H4 cannot effectively overcome absorption and disposition obstacles in vivo and thus is not amenable for direct administration in its non-derivatized form.

The (4R)-specific potency observed with H4 (or H2) underlines its unique sulfhydryl-dependent drug action. The molecular target of CPG is the platelet membrane-bound G-protein-coupled P2Y$_{12}$ receptor (P2Y$_{12}$R), which is agonized by its endogenous ligand ADP for signal transduction that leads to cell adhesion and aggregation. In recent years, P2Y$_{12}$R has been found to not only regulate platelet aggregation but also mediate a wide array of physiological and pathological processes, which include cancer metastasis, microglial response to neural injury, differentiation of T cells in autoimmune encephalomyelitis, schistosomal host response and bladder smooth muscle modulation.

As shown in FIG. 15, biochemical studies support that CPG active metabolite intercepts a conserved disulfide bond between Cys97 of helix III and Cys175 of the extracellular loop 2 in P2Y$_{12}$R, which disrupts the homooligomers and partition them out of lipid rafts. Mutation studies of individual cysteine residues in the extracellular pocket support that active metabolite adducts with Cys97, and this leads to the antagonism. Based on the detection of GSH-active metabolite mixed disulfide in vitro, it is perceived that formation of H4-Cys97 disulfide inhibits the receptor.

As depicted in FIG. 16, upon H2 incubation with 10 equivalents of ME in a mixture solvent of KPi buffer (pH 7.4) and MeOH (1/1, v/v) at 37° C. for 2 hours, H4 is already formed as a result of reversible Michael reaction, as shown in FIG. 15. LC-MS/MS studies of FIG. 17 also show that the major conjugates are the mixed disulfides of ME with H2 and H4, ME-mixD (MH$^+$=432).

In addition to these species, another major adduct ME-γA (MH$^+$=400) is also detected in the reaction mixture. This adduct is significantly more polar than the other species and shows as two overlapped peaks under chromatographic elution. High resolution mass spectral analyses reveal that ME-γA(MH$^+$=400) contains one S-atom less than ME-mixD (MH$^+$=432) (not shown). As the incubation goes, the amount of ME-γA increases, and it becomes the dominant species after 24 hours, suggesting that MEγA might be formed from MEmixD.

Overall, these results support the reaction pathway of FIG. 16: the γ-position of ME-mixD can undergo a substitution reaction with another molecule of ME to yield a "desulfurized" adduct, ME-γA; in this case, the persulfated ME functions as a leaving group. Subsequently, ME-γA was purified from the model reaction mixture, and NMR studies confirm the proposed structure.

In another H2 incubation with a large excess of ME, the di-adduct intermediate of reversible Michael addition, ME-diA (MH$^+$=510), was also detected. The detection of ME-diA confirms that the exocyclic α, β-unsaturated carboxylic acid moiety of ME-mixD can undergo Michael addition reaction, and the reversible intermediate can have appreciable half-life depending on reaction conditions.

Figure 18:
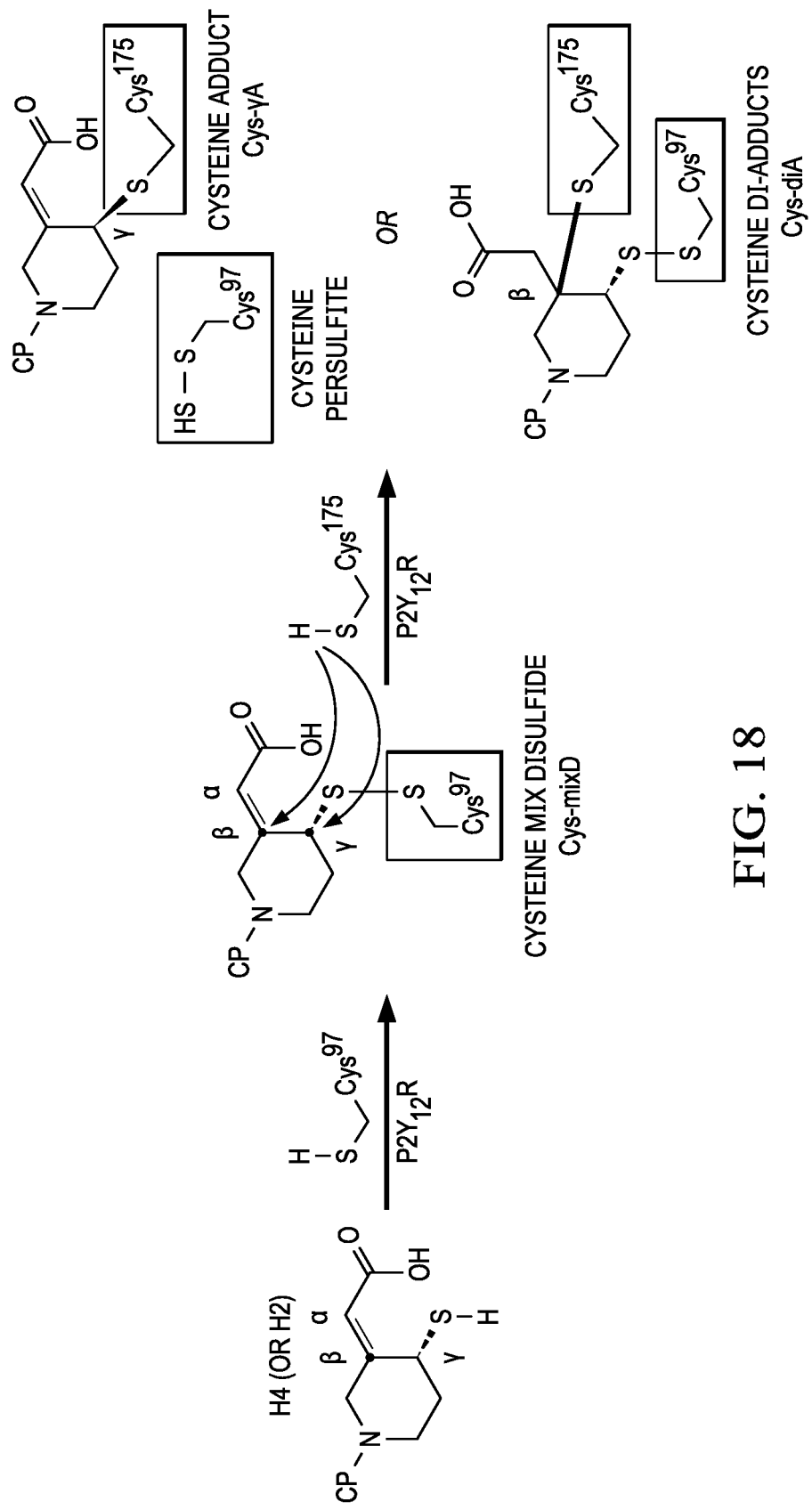
FIG. 18 is a schematic of proposed modification pathways of the extracellular Sistine residues of $P2Y_{12}R$ by active metabolites.

As depicted in FIG. 16, before the γ-mercapto forms disulfide, both the β-carbon and the γ-carbon are inert; upon the γ-disulfide formation, the β-carbon is activated for Michael addition reaction while the γ-carbon is activated for nucleophilic substitution. As depicted in FIG. 18, this "on and off" chemical reactivity of the active metabolite can shed light to its elusive drug action. In the extracellular pocket of preagonized protein, when H4 (or H2) and Cys97 form disulfide (Cys-mixD), the adjacent Cys175 can react with the "turned on" β-carbon or the γ-carbon in Cys-mixD, leading to more profound modification of the cysteine residues.

For example, when the second cysteine residue attacks the γ-carbon of Cys-mixD, the substitution reaction will yield not only a more stable cysteine adduct (Cys-γA) but also a persulfated Cys97. As persulfidation (S-sulfhydration of cysteine residue) is a known regulatory pathway of protein structure and function, the potential persulfidation of Cys97 by H4 (and Cys175) may lead to the observed receptor disruption. It is of relevance to note that a major signaling pathway of gasotransmitter hydrogen sulfide ($H_2S$) is through persulfidation of cysteine residues, which has been shown to destabilize protein monomers and disrupt the translocation of certain membrane protein; in addition, $H_2S$ has been established as an antiplatelet agent with a proposed role of antagonizing $P2Y_{12}R$ through modifying its extracellular cysteines.

Collectively, these results can be consolidated to aid future mechanistic exploration of $P2Y_{12}R$ antagonism. It is also important to note that two other cysteine residues, for example Cys17 and Cys270, are present in the same extracellular pocket, and previous mutation studies have shown that they are also involved in the antagonistic action of active metabolite. These results suggest that Cys17 and Cys270 might also be able to perform the second reaction with Cys-mixD. To sum up, upon disulfide adduct formation with Cys97, the unconventional reactivity of H4 (or H2) might compel itself to reacting with a second cysteine residue in the extracellular pocket, which not only furnishes some profound protein modification such as cysteine persulfidation, but also in return confer H4 (or H2) the observed (4R)-specific potency.

Although a pre-agonized crystal structure of $P2Y_{12}R$ is not available for assessing the proposed sequential modification, the illustrative embodiments described herein can prompt re-evaluation and reconciliation of the results obtained from previous studies; the understandings garnished here can also guide the design of new experiments to fully elucidate the mechanism of antagonism. These future efforts can lead to the development of novel antiplatelet agents for improving the onset rate of $P2Y_{12}R$ inhibition, mitigating the bleeding risks caused by receptor disruption, and overcoming irresponsiveness associated with mutated or constitutively activated protein.

Descriptions of different illustrative examples has been presented for purposes of illustration and description, and are not intended to be exhaustive or limited to the examples in the form disclosed. The different illustrative examples describe components that perform actions or operations. In an illustrative example, a component can be configured to perform action or operation described. For example, a component can have a configuration or design for a structure that provides the component an ability to perform the action or operation that is described in the illustrative examples as being performed by the component.

Many modifications and variations will be apparent to those of ordinary skill in the art. Furthermore, different illustrative examples may provide different features as compared to other examples. The examples or examples selected are chosen and described in order to explain principles of the examples, practical application, and to enable others of ordinary skill in the art to understand the disclosure for various examples with various modifications as are suited to one or more particular contemplated uses.

What is claimed is:

1. A composition of matter comprising:
a stabilized mixed disulfide derivative that includes a 4-carbon chiral center having an (R) configuration, and having a structure selected from the group consisting of:

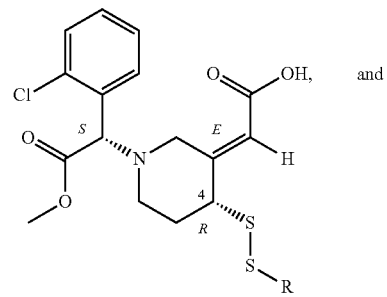

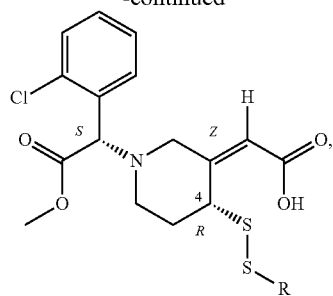
or combinations thereof,
wherein R is an unsubstituted alkyl group.
* * * * *